(12) United States Patent
Hovanec

(10) Patent No.: US 6,268,154 B1
(45) Date of Patent: Jul. 31, 2001

(54) METHOD FOR DETECTING BACTERIAL NITRITE OXIDIZER

(75) Inventor: Timothy A. Hovanec, Moorpark, CA (US)

(73) Assignee: Aquaria Inc., Moorpark, CA (US)

( * ) Notice: Subject to any disclaimer, the term of this patent is extended or adjusted under 35 U.S.C. 154(b) by 0 days.

(21) Appl. No.: 09/702,847

(22) Filed: Nov. 1, 2000

Related U.S. Application Data

(62) Division of application No. 09/216,909, filed on Dec. 21, 1998, now Pat. No. 6,207,440.
(60) Provisional application No. 60/068,492, filed on Dec. 22, 1997.

(51) Int. Cl.[7] .............................. C12Q 1/68; C12Q 1/02; C12Q 1/04; C12N 1/12; C07H 21/04
(52) U.S. Cl. .................................. 435/6; 435/29; 435/34; 435/39; 435/252.1; 536/23.1; 536/23.7; 536/24.32
(58) Field of Search .................................. 435/6, 29, 34, 435/39, 252.1; 536/23.1, 23.7, 24.32

(56) References Cited

U.S. PATENT DOCUMENTS

| | | | |
|---|---|---|---|
| 4,737,289 | 4/1988 | Castaldi et al. | 210/611 |
| 4,844,013 | 7/1989 | De Haan et al. | 119/5 |
| 4,995,980 | 2/1991 | Jaubert | 210/602 |
| 5,462,666 | 10/1995 | Kimmel | 210/602 |
| 5,462,855 | 10/1995 | Springer et al. | 435/6 |

OTHER PUBLICATIONS

Ehrich et al. Arch. Microbiol. 164:16–23, 1995.
Ehrich et al. GenEMBL Accession No. X82558, Aug. 1995.
Hovanec et al., "Nitrospira–Like Bacteria Associated with Nitrite Oxidation In Freshwater Aquaria," Applied and Environmental Microbiology, vol. 64, No.1 Jan. 1998, pp. 258–264.

Schmidt et al., "Analysis of a Marine Picoplankton Community by 16S rRNA Gene Cloning and Sequencing," Journal of Bacteriology, vol. 173, No. 14, Jul. 1991, pp. 4371–4378.
Hovanec et al., "Comparative Analysis of Nitrifying Bacteria Associated with Freshwater and Marine Aquaria," Applied Environmental Microbiology, vol. 62, No. 8, Aug. 1996, pp. 2888–2896.
Teshe et al., "Evolutionary Relationships Among Ammonia–and Nitrite–Oxidizing Bacteria," Journal of Bacteriology, vol. 126, No. 21, Nov. 1994, pp. 6623–6630.
Pommerening–Roser et al., "Phylogenetic Diversity within the Genus Nitrosomonas," System. Appl. Microbiol. 19, (1996) pp. 344–351.
Kowalchuk et al., "Analysis of Ammonia–Oxidizing Bacteria of the β Subdivision of the Class Proteobacteria in Costal Sand Dunes by Denaturing Gradient Gel Electrophoresis and Sequencing of PCR–Amplified 16S Ribosomal DNA Fragments," Applied and Env,. Microbiol,. vol. 63, No. 4., April 1997, pp. 1489–1497.
Amann et al., "Phylogenetic Identification and In Situ Detection of Individual Microbial Cells without Cultivation," Microbiol. Reviews, vol. 59, No. 1, Mar. 1995, pp. 143–169.
Schramm et al., "Identification and Activities In Situ of Nitrosospira and Nitrospira spp. As Dominant Populations in a Nitrifying Fluidized Bed Reactor," Applied and Environmental Microbiol., vol. 64, No. 5, May 1998, pp. 1878–1883.

(List continued on next page.)

Primary Examiner—Carla J. Myers
Assistant Examiner—Diana Johannsen
(74) Attorney, Agent, or Firm—Pillsbury Winthrop LLP

(57) ABSTRACT

The present invention provides an isolated bacterial strain capable of oxidizing nitrite to nitrate and a method of use thereof for preventing or alleviating the accumulation of nitrite in an aqueous medium.

4 Claims, 10 Drawing Sheets

OTHER PUBLICATIONS

Burrell et al., "Microbiology of a Nitrite–Oxidizing Bioreactor," Applied and Environmental Microbiol., vol. 64, No. 5, May 1998, pp. 1878–1883.

Juretschko et al., "Combined Molecular and Conventional Analyses of Nitrifying Bacterium Diversity in Activated Sludge: Nitrosococcus Mobilis and Nitrospira–Like Bacteria as Dominant Populations, "Applied and Environ. Microbiol. vol. 64, No. 8, Aug. 1998, pp. 3042–3051.

Hovanec et al., "Comparative Analysis of Nitrifying Bacteria Phylotpes in Freshwater and Marine Aquaria," 97th General Meeting, American Society for Microbiology, May 4–8, 1997, p. 384. (Abstract).

Hiorns et al., "Amplication of 16S Ribosomal RNA Genes of Autotrophic Ammonia–Oxidizing Bacteria Demonstrates the Ubiquity of Nitrosospiras in the Environment," (1995) 141, pp. 2793–2800.

Mobarry et al., "Phylogenetic Probes for Analyzing Abundance and Spatial Organization of Nitrifying Bacteria," Applied and Environmental Microbiol, vol. 62, No. 6, Jun. 1996, pp. 2156–2162.

Kowalchuk et al., "Analysis of Ammonia–Oxidizing Bacteria of β Subdivision of the Class Proteobacteria in Coastal . . . 16S Ribosomal DNA Fragments," Applied and Environmental Microbiol., vol. 63, No. 4, Apr. 1997, pp. 1489–1497.

Koops et al., "Classification of Eight New Species of Ammonia–Oxidizing Bacteria," Journal of General Microbiology (1991), 137, pp. 1689–1699.

Navarro et al., "Characterization of Natural Populations of Nitrobacter spp. Using PCR/RFLP Analysis of the Ribosomal Intergenetic Spacer," Arch Microbiol (1992), 157: 107–115.

Navarro et al., "Genetic Structure of Natural Populations of Nitrobacter in an Aquatic Environment," Hydrobiologia 300/301: 43–48, 1995.

Stephen et al.,"Molecular Diversity of Soil and Marine 16S rRNA Gene Sequences Related to β–Subgroup Ammona–Oxidizing Bacteria," Applied and Environmental Microbiology, vol. 62, No. 11, Nov. 1996, pp. 4147–4154.

Utaker et al., "Phylogenetic Analysis of Seven New Isolates of Ammonia–Oxidizing Bacteria Based on 16S rRNA Gene Sequences," System Appl. Microbiol. 18, 549–559 (1995).

Wagner et al., "Probing Activated Sludge with Oligonucleotides Specific for Proteobacteria: Inadequacy . . . Microbial Community Structure," Applied and Environmental Microbiol., vol. 59, No. 5, May 1993, pp. 1520–1525.

Wagner et al., "Identification and in Situ Detection of Gram–negative Filamentous Bacteria in Activated Sludge," System Applied Microbiol. 17, 405–417 (1994).

Wagner et al., "In Situ Idenification of Ammonia–Oxidizing Bacteria, " System Appl. Microbiol. 18, 251–264 (1995).

Wagner et al., "In Situ Analysis of Nitrifying Bacteria in Sewage Treatment Plants".

B.B. Ward, "Nitrification and Denitrification: Probing the Nitrogen Cycle in Aquatic Environments," Microbial Ecology (1996) 32:247–261.

Ward et al., "Phylogenetic Diversity of Natural Populations of Ammonia Oxidizers Investigated by Specific PCR Amplification," Microb Ecol (1997) 33:87–96.

Voytek et al., "Detection of Ammonium–Oxidizing Bacteria of the Beta–Subclass of the Class Proteobacteria in Aquatic Samples with the PCR," Applied and Environmental Microbiol., vol. 61, No.4, Apr. 1995, pp. 1444–1450.

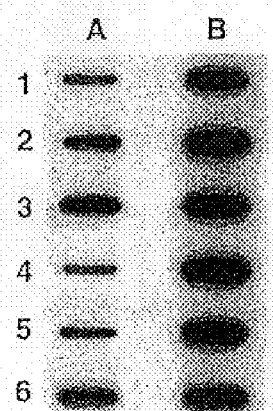 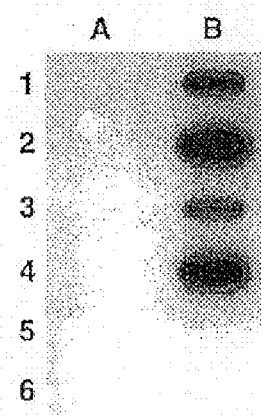 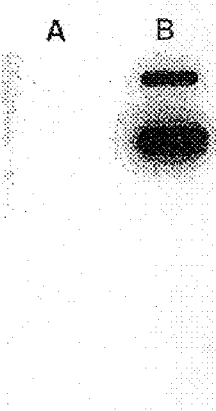
(A) S-D-Bact-0338-a-A-18    (B) S-G-Ntspa-0685-a-A-22    (C) S-*-Ntspa-0454-a-A-19

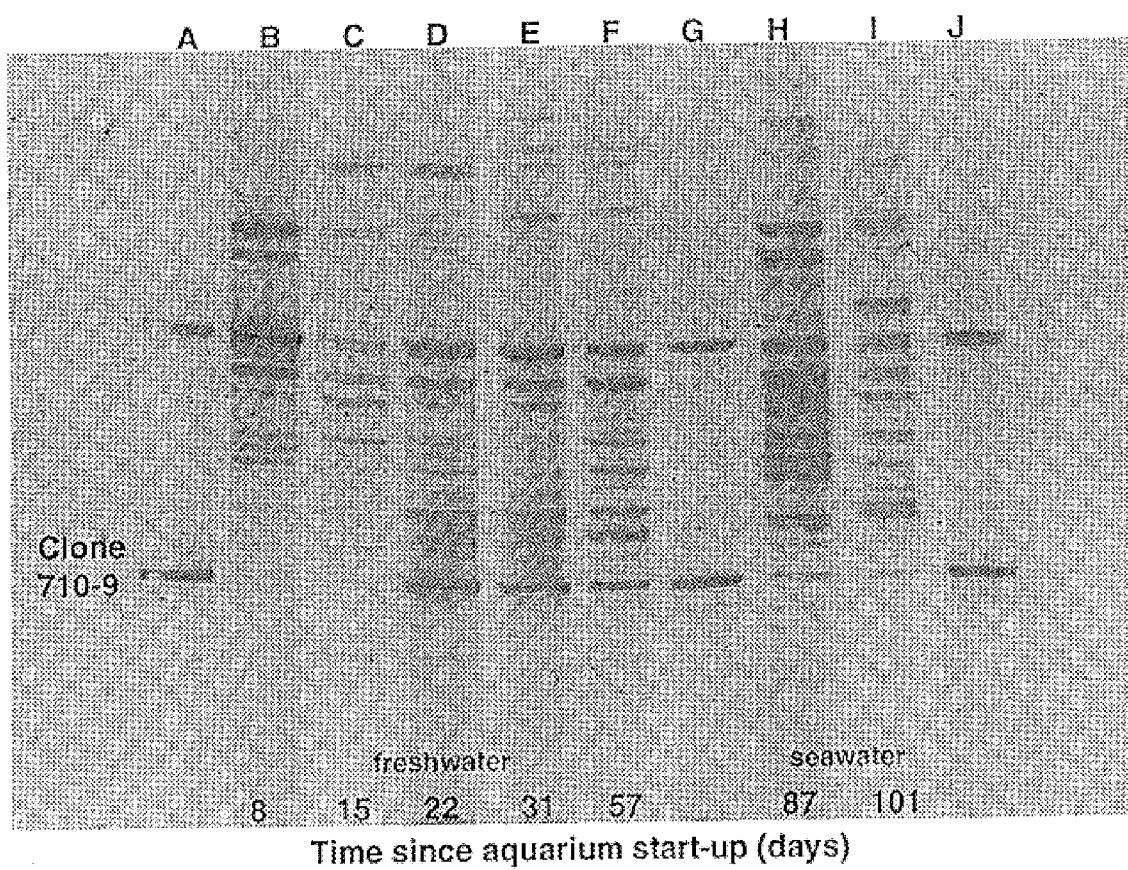

FIG. 9

```
   1  agagtttgat cctggctcag aacgaacgct ggcggcgcgc ctaatacatg caagtcgagc
  61  gagaaggtgt agcaatacac ttgtaaagcg gcgaacgggt gaggaatgca tgggtaacct
 121  accctcgagt gggaataaac tagccgaaag gttagctaat accgcatacg cttccgggac
 181  ttcggttccg gaaggaaagc aataccgtgg gtattgcgct catggatggg ctcatgtcct
 241  atcagcttgt tggtgaggta acggctcacc aaggcttcga cgggtagctg gtctgagagg
 301  acgatcagcc acactggcac tgcgacacgg gccagactcc tacgggaggc agcagtaagg
 361  aatattgcgc aatggacgaa agtctgacgc agcgacgccg cgtggggat gaaggtcttc
 421  ggattgtaaa ccctttcgg gagggaagat ggagtgggta accacttgga cggtacctcc
 481  agaagcagcc acggctaact tcgtgccagc agccgcggta atacgaaggt ggcaagcgtt
 541  gttcggattc actgggcgta caggggcgt aggcggttag gtaagcctc cgtgaaatct
 601  ccgggcctaa cccgaaagt gcagagggga ctgcttggct agaggatggg agaggagcgc
 661  ggaattcccg gtgtagcggt gaaatgcgta gagatcggga ggaaggccgg tggcgaaggc
 721  ggcgctctgg aacattactg acgctgaggc tcgaaaagcg tggggagcaa acaggattag
 781  ataccctggt agtccacgcc ttaaaactat ggatactaag tgtcggcggt ttaccgccgg
 841  tgccgcasta acgcaataag tatcccgcct gggaagtacg gccgcaaggt tgaaactcaa
 901  aggaattgac ggggcccgc acaagcggtg gagcagcatg tttaattcga cgcaacgcga
 961  agaaccttac ccaggctgga catgcaggta gtagaagggt gaaagcctaa cgaggtagaa
1021  ataccatcct gctcaggtgc tgcatggctg tcgtcagctc gtgccgtgag gtgttgggtt
1081  aagtcccgca acgagcgcaa cccctgtctt cagttactaa caggtcaagc tgagaactct
1141  ggagagactg cccaggagaa cggggaggaa ggtgggatg acgtcaagtc agcatggcct
1201  ttatgcctgg ggctacacac gtgctacaat ggccggtaca aagggctgca aacccgcgag
1261  ggggagcca atccccaaaa accggcctca gttcagattg gggtctgcaa ctcgacccca
1321  tgaaggcgga atcgctagta atcgcggatc agcacgccgc ggtgaatacg tttgttgtac
1381  ttgtacacac cgcccgtcac accacgaaag tttgttgtac ctgaagtcgt tgygccaacc
1441  gcaaggaggc aggcgcccac ggtatgaccg atgattgggg tgaagtcgta acaaggta
```

METHOD FOR DETECTING BACTERIAL NITRITE OXIDIZER

CROSS REFERENCE TO RELATED APPLICATIONS

This is a division of Application Ser. No. 09/216,909, filed Dec. 21, 1998, now U.S. Pat. No. 6,207,446 which claims priority from U.S. Provisional Application No. 60/068,492, filed on Dec. 22, 1997, the subject matter of which is hereby incorporated herein by reference.

BACKGROUND OF THE INVENTION

1. Field of the Invention

The invention relates generally to a nitrite oxidizer and specifically to a new bacterium capable of oxidizing nitrite to nitrate.

2. Background Information

The oxidation of nitrite to nitrate by chemolithoautotrophic nitrite-oxidizing bacteria (NOB) in fish culture systems, ranging from home aquaria to commercial aquaculture systems, is an important process. The accumulation of high concentrations of nitrite, toxic to fish and other aquatic organisms, is prevented by active nitrite removal by nitrifying microorganisms. Nitrite is formed in aquarium systems from the oxidation of ammonia, the principal nitrogenous waste of teleosts, by autotrophic ammonia-oxidizing bacteria (AOB). Thus, closed aquatic filtration systems usually provide a solid substratum, termed a biological filter or biofilter, to promote the growth of AOB and NOB. A variety of materials can form the substratum of a biofilter, ranging from gravel to specially engineered molded plastics. Biofilters can be submerged in the flow path of the filtration system, or can be located such that the water trickles or percolates through a medium situated in the atmosphere outside of the aquarium, before flowing back into the tank.

Traditionally, the bacteria responsible for the oxidation of ammonia and nitrite in aquaria were considered to be *Nitrosomonas europaea* and *Nitrobacter winogradskyi*, or their close relatives, respectively (Wheaton, F. W. 1977. Aquacultural Engineering. John Wiley & Sons, Inc. New York; Wheaton, F. W., J. Hochheimer, and G. E. Kaiser. 1991. Fixed film nitrification in filters for aquaculture, p. 272–303. In D. E. Brune and J. R. Tomasso (eds.), Aquaculture and Water Quality. The World Aquaculture Society, Baton Rouge, LA.). However, there is some indication that both *Nitrosomonas europaea* and *Nitrobacter winogradskyi* may not be predominant components of actively nitrifying freshwater aquaria (Hovanec, T. A. and E. F. DeLong. 1996. Comparative analysis of nitrifying bacteria associated with freshwater and marine aquaria. Appl. Environ. Microbiol. 62:2888–2896. These references, and all other references cited herein are hereby incorporated by reference.) In seawater aquaria, *Nitrosomonas europaea* and close relatives do appear to comprise a significant proportion of the total eubacterial community, but *Nitrobacter winogradskyi* was below detection limits in the study by Hovanec and Delong (1996).

Chemolithoautotrophic nitrite-oxidizing bacteria are phylogenetically diverse, occurring in several subdivisions of the Proteobacteria (FIG. 1). The most well-studied members of this group of organisms (i.e., *Nitrobacter winogradskyi* and close relatives) belong to the α subdivision of Proteobacteria (Watson, S. W. and J. B. Waterbury. 1971. Characteristics of two marine nitrite oxidizing bacteria, *Nitrospina gracilis* nov. gent nov. sp. and *Nitrococcus mobilis* nov. gen. nov. sp. Arch. Microbiol. 77: 203–230.) *Nitrospina gracilis* and *Nitrococcus mobilis*, first isolated by Watson and Waterbury, were determined to be members of the δ and γ subdivisions of the Proteobacteria, respectively (Teske, A., E. Alm, J. M. Regan, S. Toze, B. E. Rittmann, and D. A. Stahl. 1994. Evolutionary relationships among ammonia- and nitrite-oxidizing bacteria. J. Bacteriol. 176:6623–6630.) Another NOB, *Nitrospira marina*, is phylogenetically affiliated with non-nitrite-oxidizing bacteria such as *Leptospirillum ferrooxidans* (Ehrich, S., D. Behrens, E. Lebedeva, W. Ludwig, and E. Bock. 1995. A new obligately chemolithoautotrophic, nitrite-oxidizing bacterium, *Nitrospira moscoviensis* sp. nov. and its phylogenetic relationship. Arch. Microbiol. 164:16–23.) Based on phylogenetic analysis of 16S rRNA sequences, Erlich et al. proposed a new phylum within the domain Bacteria for these organisms (FIG. 1). A newly discovered nitrite-oxidizing bacterium from a freshwater environment (a corroded iron pipe in a heating system), Nitrospira moscoviensis, was recently found to be phylogenetically related to *Nitrospira marina*.

Whether in pure culture or on biofilters, NOB are slow-growing organisms with doubling times from 12 to 32 hours (Belser, L. W. and E. L. Schmidt. 1978. Diversity in the ammonia-oxidizing nitrifier population of a soil. Appl. Environ. Microbiol. 36:584–588; Carlucci, A. F. and D. H. Strickland. 1968. The isolation, purification and some kinetic studies of marine nitrifying bacteria. Exp. Mar. Biol. Ecol. 2:156–166.) Therefore, in newly set-up aquaria, ammonia and nitrite can reach concentrations toxic to fish before a sufficient biomass of AOB and NOB become established. To reduce the length of time for establishment of NOB on biofilters, commercial preparations of these organisms, in various forms of preservation, are available to seed the aquarium environment. These preparations range from essentially pure cultures of Nitrobacter species, to mixed cultures of autotrophic AOB and NOB organisms, to products which combine autotrophic nitrifying bacteria with various species of heterotrophic bacteria. Past studies have generally shown these mixes to be ineffectual, but have not elucidated specific reasons for their poor performance (Bower, C. E. and D. T. Turner. 1981. Accelerated nitrification in new seawater culture systems: effectiveness of commercial additives and seed media from established systems. Aquaculture. 24.1-9; Timmermans, J. A. and R. Gerard. 1990. Observations sur l'utilisation en etangs de suspensions bacteriennes du commerce. Bull. Fr. Peche Piscic. 316:28–30.)

Therefore, a need exists for a product containing an adequate bacterial culture to establish a sufficient biomass of nitrite-oxidizing bacteria in freshwater aquaria before the nitrite in the aquaria reaches concentrations toxic to fish.

SUMMARY OF THE INVENTION

It is an object of the present invention to provide an isolated bacterium or bacterial strain capable of oxidizing nitrite to nitrate. In a particularly preferred embodiment, the 16S rDNA of the bacterium or bacterial strain has the nucleotide sequence of SEQ ID NO:1, or a variant thereof which is at least 95% similar to SEQ ID NO:1.

The invention is also intended to include nucleic acid sequences and bacteria with sequences which are at least 90% similar, preferably 95% similar, most preferably 99% similar to SEQ ID NO:1. For the purposes of this application, "95% similar" means that single base substitutions may occur of up to 5% of the bases. By "99% similar" is meant that single base substitutions may occur of up to 1% of the bases.

In one preferred embodiment, the bacterium or bacterial strain will be in the form of a biologically pure culture of a bacterial strain capable of oxidizing nitrite to nitrate.

It is another object of the present invention to provide a mixture which includes a culture of concentrated bacteria capable of oxidizing nitrite to nitrate.

It is further object of the present invention to provide a method of alleviating the accumulation of nitrite in a medium.

The method comprises the addition to the medium of a bacterium or bacterial strain capable of oxidizing nitrite to nitrate.

It is yet another object of the present invention to provide a probe which can be used to detect and determine the quantity of bacteria capable of oxidizing nitrite to nitrate.

Accordingly, one object of the present invention is to provide a biologically pure culture of a bacterial strain capable of oxidizing nitrite to nitrate, wherein the 16S rDNA of the bacterial strain has a nucleotide sequence of SEQ ID NO:1.

Another object of the present invention is to provide a mixture comprising a concentrated bacteria capable of oxidizing nitrite to nitrate, wherein the 16S rDNA of the bacteria has a nucleotide sequence of SEQ ID 1.

A further aspect of the present invention is a method of alleviating the accumulation of nitrite in a water-containing medium. Such media include, but are not limited to, freshwater aquaria, saltwater aquaria, wastewater, wetlands, and other environments in which it is found desirable to reduce the nitrite load. The method comprises a step of placing into the medium a sufficient amount of bacteria capable of oxidizing nitrite to nitrate to alleviate the accumulation of nitrite in the medium. In a preferred embodiment of the method, the 16S rDNA of the bacteria has a nucleotide sequence of SEQ ID NO:1.

A further aspect of the present invention is a DNA probe and a method for detecting and determining the quantity of bacteria capable of oxidizing nitrite to nitrate in a medium containing bacteria gravel.

The present invention provides a number of advantages. As explained in greater detail below, the bacteria of the present invention can effectively alleviate or eliminate the accumulation of nitrite in a medium, particularly in freshwater aquaria. The DNA probes of the present invention and the method of use of the probes in accordance with the present invention provide an effective tool for one to detect and measure the existence of a bacterial strain which is capable of oxidizing nitrite to nitrate in a given medium.

The bacteria of the present invention are well suited for use in freshwater aquaria, seawater aquaria and wastewater to alleviate the accumulation of nitrite. They can also be used in a bioremediation process to reduce the level of pollution caused by nitrite.

In the use of the bacteria in accordance with the present invention, the bacteria may be placed on substrate such as a rotating biological contactor (RBC), a biofilter unit, or other suitable substrate. The bacteria can be used in the form of powder, liquid and solid (for example, freeze-dried) form. The compositions may include preservatives, nutrients and the like, as desirable to stabilize the bacteria and promote growth in the medium. The compositions may also include other bacterial strains. The inclusion of such additional strains may be desirable, for example, for removal of other pollutants or undesirable substances which may be found in the medium.

BRIEF DESCRIPTION OF THE DRAWINGS

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which:

FIGS. 3A–3C show the specificity of the nucleotide probes targeting nitrite-oxidizing bacteria (NOB) of the Nitrospira Group and the 710-9 clone identified in this study. Probe order is Eubacterial probe S-D-Bact-0338-a-A-18 (A), Nitrospira-like NOB probe S-G-Ntspa-0685-a-A-22 (B), and Nitrospira-like NOB probe S-*-Ntspa-0454-a-A-19 (C), with rRNA, transcribed RNA (trRNA) or PCR amplified rDNA, in the following arrangement: slot a-1, *Comamonas testosteroni*; slot a-2, *Alcaligenes eutrophus*; slot a-3, *Alcaligenes faecalis*; slot a-4, *Comamonas acidovorans*; slot a-5, *Nitrobacter winogradskyi* (rDNA); slot a-6, *Nitrobacter agilis* (rDNA); slot b-1, clone 710-9 (rDNA); slot b-2, clone 710-9 (trRNA); slot b-3, *Nitrospira marina* (rDNA); slot b-4, *Nitrospira marina* (trRNA); slot b-5, *Nitrospina gracilis*; slot b-6, *Shewanella putrefaciens*.

FIG. 5 shows denaturing gradient gel electrophoresis (DGGE) time series profile from a biofilm of a freshwater 15 aquarium during the establishment of nitrification. The aquarium was switched to seawater on day 80. Lanes A, G and J contain two clones including Clone 710-9, a putative nitrite-oxidizing bacterium showing close similarity to the Nitrospira group. The band corresponding to this organism first appears with significant intensity on Day 22. Lanes B, C, D, E, and F are sampling dates before the switch to seawater. Lanes H and I are sampling dates after the switch to seawater. The water chemistry for various forms of nitrogen in this aquarium is shown in FIG. 4.

FIG. 9 is the nucleotide sequence of the 16S rDNA of a bacterial strain of the present invention (nucleotides 65–1592 SEQ ID NO:1).

DETAILED DESCRIPTION OF THE INVENTION

Figure 1:
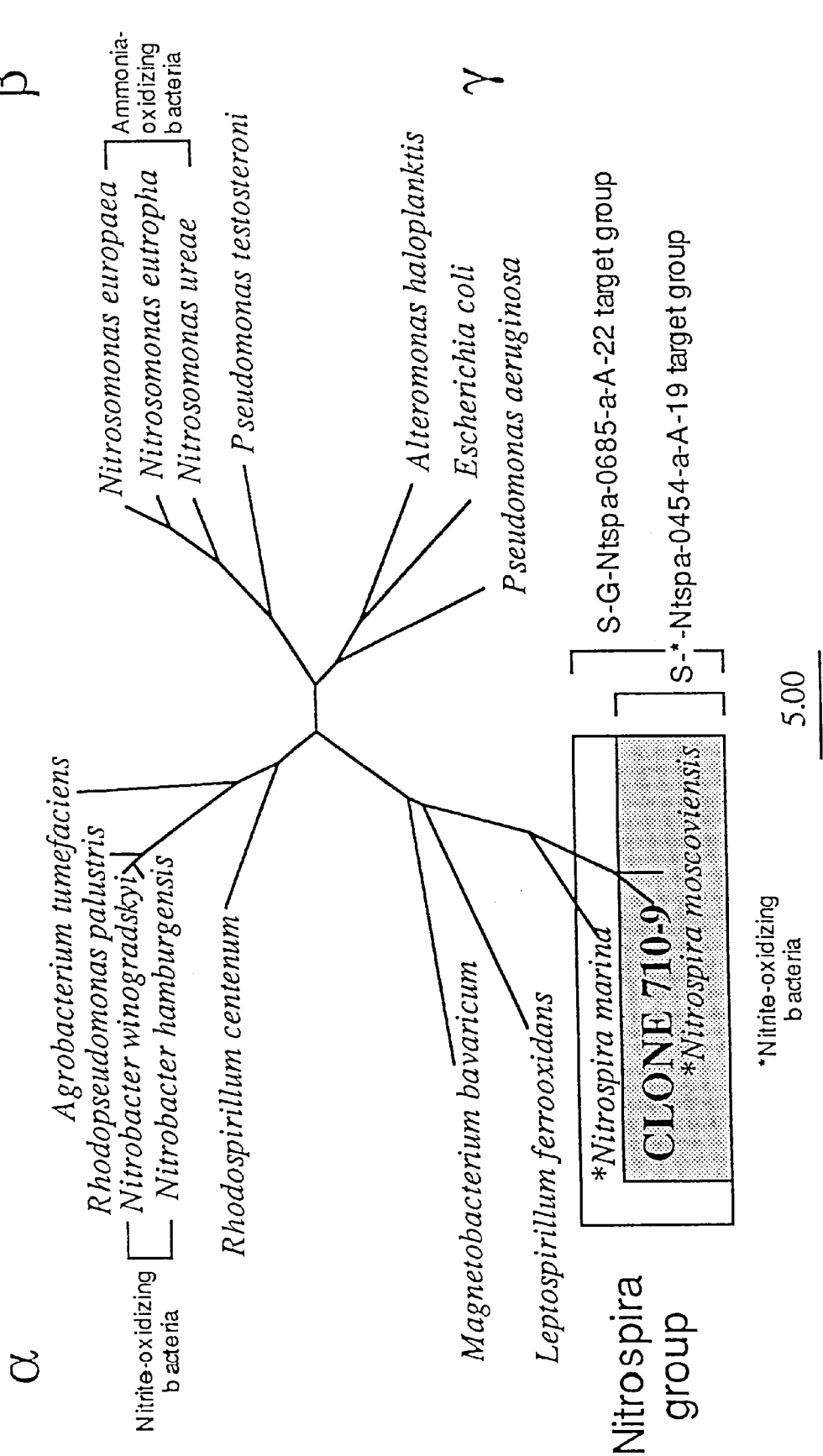
FIG. 1 shows phylogenetic relationships of autotrophic nitrite-oxidizing bacteria (NOB) in the Proteobacteria subdivision and the Nitrospira Group. Clone 710-9, a rDNA clone originating from aquaria with active nitrite-oxidizing bacterial populations, is most similar to nitrite-oxidizing bacteria of the Nitrospira group. The specificity of two nucleotide probes designed for Nitrospira spp. are indicated by the boxed sections.

The present invention is based on the surprising discovery of a novel bacterial strain which is responsible for nitrite oxidization in freshwater aquaria.

The present invention provides an isolated bacterial strain or a biologically pure culture of a bacterial strain capable of oxidizing nitrite to nitrate, wherein the 16S rDNA of the bacterium strain has a nucleotide sequence of SEQ ID NO:1, nucleotides 65–1592 as shown in FIG. 9. For the purposes of the present invention, an isolated bacterial strain is one which has undergone some degree of purification from its natural environment. A culture of a bacterium considered to be biologically pure if at least 20% of the bacteria are from one bacterial strain. However, it is preferable if the culture is at least 33% pure, more preferable at least 45% pure and most preferable at least 90% pure.

The bacterial strain of the present invention may also be combined with other species of bacteria, nutrients, and/or other components to provide a composition for maintaining or purifying water-containing media. It may be desirable, for example to combine the bacteria of the present invention with bacteria capable of removing other pollutants or undesirable compounds from water-containing media. Examples of such bacteria include ammonia-oxidizing bacteria (chemolithoautotrophic bacteria which oxidize ammonia to nitrite), heterotrophic bacteria (which mineralize organic material into ammonia), and other bacteria which will be known to those of skill in the art. Ammonia-oxidizing bacteria, for example, are known from the beta subdivision of the Proteobacteria, for example species of the genera Nitrosomonas and Nitrosospira. Nitrate-reducing bacteria are known from the genera Azoarcus, Pseudomonas and Alcaligenes. Heterotrophic microorganisms are known from the genera Bacillus, Pseudomonas, and Alcaligenes. Such are available from known sources (e.g. American Type Culture Collection, 10801 University Blvd., Manassas Va. 20110, USA) or could be isolated directly from aquaria biofilters.

For example, the bacterial strain of the present invention could be combined with ammonia-oxidizing bacteria such that ammonia present in the water system would be oxidized to nitrite and the nitrite oxidized to nitrate. Another example would be to combine the bacterial strain of the present invention with aerobic or anaerobic denitrifying bacteria. In this case, the nitrate which is produced by the bacterial strain of the present invention would be reduced to dinitrogen or other nitrogen based products. A third example would be combine the bacterial strain of the present invention with heterotrophic bacteria which mineralize organic matter into simpler inorganic substances which, subsequently, can be utilized as substrates by ammonia-oxidizing bacteria and/or the bacterial strain of the present invention.

The isolated bacterial strains of the present invention comprise bacteria which are similar to members of the Nitrospira group in that they can be detected with oligonucleotide probes having the sequence 5'-CACCGGGAATTCCGCGCTCCTC'3' (SEQ ID NO:2) or 5'-TCCATCTTCCCTCCCGAAAA-3' (SEQ ID NO:3).

The present invention also provides a mixture comprising a concentrated bacterial strain capable of oxidizing nitrite to nitrate, wherein the 16S rDNA of the bacterium has a nucleotide sequence of SEQ ID NO:1. According to the invention, the bacterial strain is considered to be concentrated if the bacterial strain occurs in a concentration which is higher than its concentration occurred in nature. In general, the concentration of the bacterial strain will be at least 20% of the total cells in the sample as determined by standard techniques such as molecular probing using fluorescent in situ hybridization techniques, which will be known to those skilled in the art, using appropriate controls and enumeration methods. More preferably, the concentration of the bacterial strain would be 33% or greater of the total cells, even more preferably 45%, and most preferably 90% or greater of the total cells.

It is understood that the bacterial strain, and the mixture of the present invention can be in a form of powder, liquid, a frozen form, and a freeze-dried form. Such forms include, but are not limited to:

(1) a liquid form, wherein the strain is in a liquid solution containing inorganic salts or organic compounds such that the viability of the cells is not destroyed during the course of storage;

(2) a frozen form, wherein the strain in a liquid mixture as above, optionally including cryoprotectant compounds to prevent cell lysis, is frozen and stored at a temperature at or below 32 F;

(3) a powder form, which has been produced by freeze-drying or other means, wherein the dehydrated form of the strain or mixture can be stored at normal room temperature without loss of viability.

Obtaining a proper form of the bacterial strain and the mixture of the present invention is well within the skill in the art in view of the instant disclosure. It is also understood that the bacterial strain and the mixture of the present invention can be used alone, or in combination with other components. Examples of such components include, but are not limited to, ammonia-oxidizing bacteria, heterotrophic ammonia-oxidizing bacteria, heterotrophic nitrite oxidizing bacteria, and the like. All of the forms of the biologically pure bacterial strain may also contain nutrients, amino acids, vitamins and other compounds which serve to preserve and promote the growth of the bacterial strain. The bacterial strain and the mixtures and compositions of the present invention can be used in freshwater aquaria, seawater aquaria, and wastewater to alleviate the accumulation of nitrite. They can also be used in a bioremediation process to reduce the level of pollution caused by the nitrite. A biomediation process, also called bioaugmentation, includes, but is not limited to, the supplemental addition of microorganisms to a system (e.g. a site where biological or chemical contamination has occurred) for the purposes of promoting or establishing biological and/or chemical processes which result in the change of one or more forms of chemical compounds present in the original system.

Accordingly, one aspect of the present invention provides a method of alleviating the accumulation of nitrite in a medium. The method includes a step of placing into the medium a sufficient amount of a bacterial strain capable of oxidizing nitrite to nitrate to alleviate the accumulation of nitrite in the medium, wherein the 16S rDNA of the bacterium strain has a nucleotide sequence of SEQ ID NO:1. The amount of the bacterial strain is sufficient if the added bacteria can alleviate or prevent the accumulation of nitrite in the medium. In general, the addition of the bacterial strain of the invention to a freshwater or saltwater aquarium is expected to reduce the maximum nitrite concentration by at least 30% over the level which would be attained in the absence of the bacterial strain.

It will be appreciated that the actual levels achieved in a given setting will be a function of the size and contents of the system, i.e. the number of fish, plants, etc. contained in the system. In a newly set up 37 liter aquarium with 10 adult fish, the nitrite concentration may reach 8 mg/l or higher without addition of the bacterial strain, whereas the maximum level can be reduced to about 3 mg/l by addition of the bacterial strain. In general, the maximum nitrite concentration would not be expected to exceed 5 mg/l if the bacterial strain of the invention is added to such a system. When the system reaches a steady state, the nitrite levels drop back to below 0.25 mg/l, a process which occurs more rapidly when the bacterial strain of the invention is present.

In one embodiment of the present invention, the bacterial strain of the present invention is placed directly into a medium such as, but not limited to, freshwater aquaria, seawater aquaria, and wastewater. Preferably, the bacteria can be first grown on a rotating biological contactor and then placed into a medium. In a different embodiment, the bacteria of the present invention can be placed on a biofilter unit contained in a medium.

As used herein, the term "aquarium" is intended to mean a container which may be made of, in combination or in its entirety, but not limited to, glass, plastic, or wood that holds water and in which living aquatic organisms (such as fish, plants, bacteria and invertebrates) are placed, and the contents thereof. An aquarium may be for the purposes of displaying aquatic organisms, for their short or long-term holding, for scientific study, for transportation and other purposes. A freshwater aquarium is generally an aquarium in which the liquid medium has a salinity of less than 15 parts per thousand. A saltwater aquarium is generally an aquarium in which the liquid medium has a salinity of more than 15 parts per thousand. The term "aquarium water" is used to refer to the medium which is contained within the aquarium, and its associated filter systems, in which the aquatic organisms reside. Aquarium water may contain a wide range of inorganic or organic chemical substances and, therefore, may have a wide range of concentration of such parameters as salts, pH, total dissolved solids, and temperature to name a few.

As used herein, "wastewater" generally refers to a liquid medium which is the product of an industrial or human process. It may need to be treated by one or more filtration methods to render it less harmful to the environment such that it conforms to discharge standards as determined by a governmental agency. A wastewater may also be recycled such that it is not discharged to the environment.

As used herein, "biofilter" generally refers to a filter type whose purpose is to promote the growth of microorganisms, or provide a substrate for the attachment and growth of microorganisms. A biofilter may be part of an aquarium filtration system or a wastewater filtration system. As used herein, the term "rotating biological contactor" generally refers to a type of biofilter which rotates in the water or medium. It may be completely or partially submerged in the water or medium. Persons skilled in the art will recognize rotating biological contactors as embodied in U.S. Pat. Nos. 2,085,217; 2,172,067; 5,423,978; 5,419,831; 5,679,253; 5,779,885 and all continuations, improvements and foreign counterparts, the same being commonly held by the assignee of the present invention and each respectively expressly incorporated herein by reference.

As used herein, "filter floss" refers to irregularly shaped natural or synthetic multi-stranded material which may serve as a biofilter, a mechanical filter or a combination of these.

As used herein, "aquarium gravel" refers to a substrate commonly placed inside, on the bottom, of an aquarium. It may be composed of irregular or regular shaped pieces of rock, coral, plastic or other material. It may serve as a biofilter, a mechanical filter, for decorative purposes or a combination of these.

As used herein, the term "filter sponge" refers to a natural or synthetic material which when used in an aquarium or as part of an aquarium filtration system may serve as a mechanical filter or a biofilter or both.

As used herein, "plastic filter media" refers to a man-made material which serves as a biofilter or mechanical filter or both. It may be plastic molded or injected molded.

The present invention provides a nucleotide probe for detecting and measuring the amount of bacteria of the present invention which are present in a medium. The probe has a nucleotide sequence of 5'-CACCGGGAATTCCGCGCTCCTC'3' (SEQ ID NO:2) or a nucleotide sequence of 5'-TCCATCTTCCCTCCCGAAAA-3' (SEQ ID NO:3). The nucleotide probes of the present invention can be synthesized by methods which are known in the art.

The nucleotide probes of the present invention can be labeled by any labels that are detectable. Examples of suitable labels include, but are not limited to, radioactive labels, fluorescent labels and the like. Suitable labeling materials are commercially available and would be known to those of ordinary skill in the art. The methods of labeling an oligonucleotide or a polynucleotide are also known to those of ordinary skill in the art. (See, for example, Sambrook, J., E. F. Fritsch, and T. Maniatis. Molecular Cloning-A Laboratory Manual, $2^{nd}$ edition, 1989, Cold Spring Harbor Press.)

The nucleotide probes of the present invention can hybridize with 16S rDNA of the bacterial strain of the present invention. Accordingly, the nucleotide probes of the present invention are well suited for use in a method for detecting and determining the quantity of bacteria of the present invention.

In one aspect of the present invention, it is provided a method for detecting and determining the quantity of bacteria capable of oxidizing nitrite to nitrate in a medium, wherein the 16S rDNA of the bacteria has a nucleotide sequence of SEQ ID NO: 1. The method includes the steps of:

(a) providing a detectably labeled probe of the present invention;

(b) isolating total DNA from a medium;

(c) exposing the isolated total DNA to the detectably labeled probe under conditions under which the probe hybridizes to only the nucleic acid of the bacteria, wherein the 16S rDNA of the bacteria has a nucleotide sequence of SEQ ID NO:1;

(d) detecting and measuring the hybridized probe for detecting and measuring the quantity of the bacteria.

The medium can be aquarium water, wherein the DNA is isolated therefrom. The medium can also contain a material selected from a group consisting of aquarium gravel, sponge filter material, filter floss, and plastic filter media, but is not considered to be limited to these. Accordingly, the DNA can be isolated from the above and other sources where such bacteria may be expected to be found.

The detection method of the present invention provides an effective tool for one to monitor and detect the occurence of bacteria capable of oxidizing nitrite to nitrate in a medium. The method also provides a tool for one to check the commercial additives to determine the effectiveness of the additives, particularly in freshwater aquaria, by measuring the occurrence or the amount of the bacteria of the present invention.

Examples of the embodiments of the present invention are set forth below in detail.

Materials and Methods

Nucleic acid sampling and extraction. For rRNA extractions from aquarium gravel, individual gravel samples (10 g) were placed in a polypropylene tube and covered with 2.5 ml of low-pH buffer (50 mM sodium acetate, 10 mM disodium EDTA) and processed as previously described (Hovanec, T. A. and E. F. DeLong. 1996. Comparative analysis of nitrifying bacteria associated with freshwater and marine aquaria. Appl. Environ. Microbiol. 62:2888–2896.). For DNA extraction, gravel samples were resuspended in cell lysis buffer (40 mM EDTA, 50 mM Tris-HCl, 0.75 M sucrose) and processed as described previously. Samples were stored at −20° C. until extraction.

DNA was quantified by Hoechst type 33258 dye binding and fluorometry (DynaQuant 200, Hoefer Pharmacia Biotech Inc., San Francisco, Calif.). rRNA was quantified by measuring absorbance at 260 nm (Perkin Elmer, Lambda 3B, The Perkin-Elmer Corporation, 761 Main Avenue, Norwalk, Conn. 06859), assuming that 1 A260 unit corresponds to 40 µg/mL RNA.

Clone libraries of PCR amplified rRNA genes. Clone libraries were derived from nucleic acid extracts of aquarium samples. Bacterial ribosomal RNA gene fragments were amplified with the primers S-D-Bact-0011-a-S-17 (8f; GTT TGA TCC TGG CTC AG) (SEQ ID NO:4) and 1492r (eubacterial; GGT TAC CTT GTT ACG ACT T) (SEQ ID NO:5) or S-*-Univ-0519-a-A-18 (519r; GWA TTA CCG CGG CKG CTG) (SEQ ID NO:6). PCR conditions, cycle parameters, and reaction components were as previously described (DeLong, E. F. 1992. Archaea in coastal marine environments. Proc. Natl. Acad. Sci. USA 89:5685–5689.) PCR products were evaluated by agarose gel electrophoresis. PCR fragments were cloned with a TA Cloning kit (Invitrogen, Carlsbad, Calif.), as described in the manufacturer's directions.

DGGE analysis and profiling. For DGGE analysis, rDNA fragments were amplified using the forward 358f (eubacterial; CCT ACG GGA GGC AGC AG) (Seq ID NO:7) with a 40-bp GC-clamp on the 5' end as described by Murray et al. (Murray, A. L., J. T. Hollibaugh, and C. Orrego. 1996. Phylogenetic compositions of bacterioplankton from two California estuaries compared by denaturing gradient gel electrophoresis of 16S rDNA fragments. Appl. Environ. Microbiol. 62:2615–2620), and the reverse primer S-*-Univ-0519-a-A-18 (519r; GWA TTA CCG CGG CKG CTG) (SEQ ID NO:6). PCR was performed on a Stratagene Robocycler Gradient 96 (La Jolla, Calif.) using the manufacturer's reagents. PCR conditions included a hot start (80° C.) and a touchdown procedure. Initial denaturation at 94° C. for 3 minutes was followed by a denaturation at 94° C. for 1 min. a touchdown annealing from 65° C. to 55° C. for 1 min 29 sec (the annealing time during the touchdown increased by 1.4 see per cycle), and primer extension at 72° C. for 56 see (the extension time was increased 1.4 seconds per cycle). The final temperature series of the above thermal cycle was repeated for 20 total cycles, followed by a final extension at 72° C. for 5 min. Amplicons were examined by agarose gel electrophoresis.

DGGE was performed with a Bio-Rad D-GENE System (Bio-Rad Laboratories, Hercules, Calif.). All gels were 8.5% acrylamide/Bis using Bio-Rad reagents (D GENE Electrophoresis Reagent Kit, Bio Rad Laboratories, Hercules, Calif.). Gel gradients were poured using Bio-Rad reagents (D GENE Electrophoresis Reagent Kit, Bio Rad Laboratories, Hercules, Calif.) with a denaturing gradient of 20 to 60% (where 100% denaturant is a mixture of 40% deionized formamide and 7 M urea) and the Bio-Rad gradient delivery system (Model 475, Bio Rad Laboratories, Hercules, Calif., USA). All gels were run at 200 volts for 6 hours. Gels were visualized in one of two ways. For visualization and recovery of discrete DNA bands, gels were first stained for 10 minutes in 250 ml of 1× TAE buffer in which 100 µl of ethidium bromide (1 mg/ml) was added, then washed for 10 minutes in 1× TAE buffer. For documentation purposes some gels were stained in Vistra Green (diluted 1:10,000) (Molecular Dynamics, Sunnyvale, Calif.) for 20 minutes, followed by a 20 minute wash in 1 X TAE buffer, and then scanned using a FluorImager SI (Molecular Dynamics, Sunnyvale, Calif.).

Individual bands were excised from the DGGE gels using alcohol sterilized scalpels. Extraction of DNA from the gel followed the methods of Ferris et al. (Ferris, M. J., G. Muyzer, and D. M. Ward. 1996. Denaturing gradient gel electrophoresis profiles of 16S rRNA-defined population inhabiting a hot spring microbial mat community. Appl. Environ. Microbiol. 62:340–346.) The excised band was placed in a sterile 2 ml screw cap tube with 500 µl sterile deionized water. The tubes were half-filled with glass beads (cat. no. 11079–101, BioSpec Products Inc., Bartlesville, Okla.) and placed in a mechanical bead beater (Mini-beadbeater-8, BioSpec Products Inc., Bartlesville, Okla.) for 3 minutes at the highest setting. The processed DNA remained in the tubes at 4° C. overnight. After overnight storage, the tubes were centrifuged at 3,200×g for 8 minutes at 4° C. to concentrate the gel fragments. The supernatant was transferred to a clean eppendorf tube.

To check the extraction efficiency, the supernatant was reamplified with the DGGE primers and re-analyzed by DGGE. An extraction was considered acceptable if it yielded a single band in DGGE analysis which co-migrated with the original DGGE band in the mixed population sample.

Oligonucleotide probe development and hybridization procedures. Two oligonucleotide probes were designed which specifically hybridize with *Nitrospira marina*, *Nitrospira moscoviensis*, and the Nitrospira-like rRNA gene sequence isolated in this study from biofilters. One probe (S-G-Ntspa-0685-a-A-22) targets the biofilter-derived Nitrospira-like bacterium, and both *Nitrospira marina* and *Nitrospira moscoviensis*. The second probe (S-*-NTspa-0454-a-A-19) targets the biofilter-derived Nitrospira-like bacterium and its closest cultivated relative, *Nitrospira moscoviensis* (FIG. 1). Probe matches were initially screened using BLAST (Altschul, S. F., W. Gish, W. Miller, E. W. Myers, and D. J. Lipman. 1990. Basic local alignment tool. J. Mol. Biol. 215:403–410) and CHECK_PROBE (Maidak, B. L., N. Larsen, M. J. McCaughey, R. Overbeek, G. J. Olsen, K. Fogel, J. Blandy, and C. R. Woese. 1994. The ribosomal database project. Nucleic Acids Res. 22:3485–3487.) Probes were synthesized by Operon Tech, Inc. (Alameda, Calif.). The nucleotide sequences and positions of the probes are shown in Table 1.

E. F. DeLong. 1996. Comparative analysis of vitrifying bacteria associated with freshwater and marine aquaria. Appl. Environ. Microbiol. 62:2888–2896.) Methods for determining the relative amount of rRNA-specific hybridization signal from each probe were the same as previously described (Hovanec, T. A. and E. F. DeLong. 1996. Comparative analysis of nitrifying bacteria associated with freshwater and marine aquaria. Appl. Environ. Microbiol. 62:2888–2896.)

Sequencing. Sequencing of SSU rDNA excised from DGGE gels or clones was performed directly using Sequenase 2.0 (United States Biochemical, Cleveland, Ohio).

TABLE 1

The nucleotide sequences and positions of oligonucleotide probes for nitrite-oxidizing bacteria.

| Probe[a] | Position (nucleotides)[b] | Base Sequence (5' to 3') | Td (° C.)[c] | Wash temp (° C.) | Targeted Group | Nontarget bacteria with exact match to probe sequence |
|---|---|---|---|---|---|---|
| S-G-Ntspa-0685-a-A-22 | 664–685 | CAC CGG GAA TTC CGC GCT CCT C (SEQ ID NO: 2) | 63.0 | 60.0 | *Nitrospira moscoviensis, N. marina* and 710–9 clone | None |
| S-*-Ntspa-0454-a-A-19 | 435–454 | TCC ATC TTC CCT CCC GAA AA (SEQ ID NO: 3) | 58.5 | 56.0 | *Nitrospira moscoviensis* 710–9 clone | None |

[a]probe names designated using the standard proposed by Alm et al. 1996 (Alm, E. W., D. B. Oerther, N. Larsen, D. A. Stahl, and L. Raskin. 1996. The oligonucleotide probe database. Appl. Environ. Microbiol. 62:3557–3559)
[b]*Escherichia coli* numbering
[c]Temperature of dissociation(Td) is defined as temperature at which 50% of the bound probe is released from the homologous hybrid Since no pure rRNA of the biofilter-derived Nitrospira-like bacterium is yet available, in vitro-transcribed 16S rRNA was used as template for temperature of dissociation (Td) determinations and as a control in hybridization experiments. In vitro-transcribed 16S rRNA was synthesized as described by Polz and Cavanaugh (Polz, M. F. and C. M. Cavanaugh. 1997. A simple method for quantification of uncultured microorganisms in the environment based on in vitro transcription of 16S rRNA. Appl. Environ. Microbiol. 63:1028–1033.)

The dissociation temperature (Td) of the oligonucleotide probes was determined by measuring the amount of probe eluted over a series of increasing wash temperatures (Raskin, L., J. M. Stromley, B. E. Rittmann, and D. A. Stahl. 1994. Group-specific 16S rRNA hybridization probes to describe natural communities of methanogens. Appl. Environ. Microbiol. 60:1232–1240.) For these tests, 200 ng of template was immobilized on a nylon membrane (Hybond-N, Amersham) and hybridized overnight at 45° C. with $^{32}$P-labelled probe. After hybridization, the membrane was washed at room temperature in 1× SET (150 mM NaCl, 1 mM EDTA, 20 mM Tris; pH 7.8) and 1% SDS for 30 minutes on a shaker table. Individual filter strips were then placed in a 0.5 ml eppendorf tube containing 500 $\mu$l 1× SET/1% SDS preheated to the initial test temperature. The eppendorf tubes were placed in a thermal cycler (Perkin Elmer) and incubated for 30 minutes. The membrane was transferred to a new eppendorf tube containing 1× SET/1% SDS, and the temperature increased, and held at the elevated temperature for 30 minutes. After each wash, the wash buffer was transferred to a scintillation vial containing 3 ml scintillation cocktail (Liquiscint, National Diagnostics, Atlanta, Ga.) mixed, and the radioactivity quantified by liquid scintillation counting. Each profile was performed in duplicate. rRNA from aquaria was slot blotted and quantified using nucleic acid probes developed in this and an earlier study (Hovanec, T. A. and E. F. DeLong. 1996. Comparative analysis of nitrifying bacteria associated with freshwater and marine aquaria. Appl. Environ. Microbiol. 62:2888–2896.) under conditions previously described (Hovanec, T. A. and Experimental Aquarium Systems. Three sets of experiments were run in aquaria to a) study the establishment of nitrifying bacteria and b) determine the effect of a bacterial additive. New aquaria, filter systems, and gravel were used for each test. Samples of aquarium water for the three tests were analyzed for ammonia (gas diffusion membrane method), nitrite (azo dye method) and nitrate (cadmium reduction-azo dye method) by flow injection analysis as previously described (Hovanec, T. A. and E. F. DeLong. 1996. Comparative analysis of nitrifying bacteria associated with freshwater and marine aquaria. Appl. Environ. Micrbiol. 62:2888–2896.).

Bacterial Additive Test.

Six all-glass aquaria were established with an airlift undergravel filtration system (Model KF720, Neptune Products, Moorpark, Calif.) in a temperature controlled laboratory (mean air temperature 26.0° C.±1.5° C.). The aquaria were covered with glass lids but not illuminated other than room ceiling lights which were on a 14 hr:10 hr light:dark cycle. 6.8 kg of natural aquarium gravel (Kaytee Products, Irwindale, Calif.) was placed on top of the filtration plate. 30 l of city tap water, passed through activated carbon, was added to each aquarium. Filtered air was supplied to each aquarium from a common air source. 6 fish (Danio aequipinnatus) were placed in each aquarium and fed 0.5 g fish feed (Aquarian, Kal Kan Foods, Vernon, Calif.) daily over two feedings. Three of the aquaria (the treatment group) were each dosed with 8 ml of bacterial additive (Cycle®, Rolf C. Hagen Inc., Mansfield, Mass.) on the first day and once every 7 days afterwards for an additional 3 weeks. The other three aquaria were the control group and did not receive an additive.

Two samples of 10 g of gravel were collected from each aquarium on a weekly basis and nucleic acids extracted and analyzed as described above.

Time of NOB Appearance.

Three all-glass aquaria were established as described above. 34 l of city tap water, passed through activated carbon, was added to each aquarium which contained 4.53 kg of gravel. Initially, 0.71 mmol of filter-sterilized (0.2 $\mu$m) ammonium chloride was added to each tank, followed by an additional dosing of 5.0 mmoles $NH_4Cl$ on the fourth day. On days 10, 15, 18, 23 and 30 further ammonia additions of 8.9 mmoles were made to each aquarium. During the test a total of 50.4 mmoles of ammonia was added to each aquarium. Water samples were collected daily.

Two 10 g samples of gravel were collected from each aquarium daily for 33 days. To one sample 2 ml of lysis buffer was added and the sample frozen (–20° C.) until rDNA was extracted by previously described methods. rDNA was subjected to DGGE after undergoing the PCR with the primers and conditions stated earlier. The other sample was preserved with 2 ml of bead beating buffer.

Time series.

Three aquaria were set-up as previously described with 4.53 kg of gravel and filled with 30 l of city water which had been passed through activated carbon. The test was run for 138 days during which the aquaria were individually dosed with 8.9 mmoles of filter-sterilized (0.2 $\mu$m) ammonia (as ammonium chloride) on the first and second day of the test. From days 12 to 78 of the test, further additions of 8.9 mmoles ammonia were done on average every 3 days. A total of 246 mmoles of ammonia was added to each tank during the test. The water was sampled three times a week for chemical analysis. The aquaria were run for 80 days with freshwater at which time they were switched to seawater (32 ppt) by draining and refilling with water mixed with artificial seasalts (Marineland Commercial Aquariums, Moorpark, Calif.). After the switch the aquaria were run for an additional 57 days.

Nucleotide sequence and Depository accession numbers. The nucleotide sequence has been deposited in the GenBank database under accession number AF035813 for Clone 710-9. Clone 710-9 has been deposited under the Budapest Treaty at the American Type Culture Collection,10801 University Blvd., Manassas, Va. 20110-2209, USA, as accession no. 202186 on Dec. 17, 1998.

The mineral medium formula used to grow the bacterial strain of the present invention: In one embodiment of the present invention, one can isolate and grow the bacteria strain of the present invention in an isolation medium disclosed by Ehrich et. al. (S. Ehrich, D. Behrens, E. Lebedeva, W. Ludwig, and E. Bock, A new obligatory chemolithoautotrophic, nitrite-oxidizing bacterium, *Nitrospira moscoviensis* sp. *nov.* and its phylogenetic relationship. Arch Microbial (1995) 164:16–23.) One example of such isolation media has the following formula:
7.25 mmol sodium nitrite,
0.07 mmol calcium carbonate,
8.56 mmol sodium chloride,
0.25 magnesium chloride,
0.86 mmol potassium phosphate,
0.15 $\mu$mol magnesium sulfate,
0.79 $\mu$mol boric acid,
0.15 $\mu$mol zinc sulfate,
0.03 $\mu$mol molybdic acid,
0.10 $\mu$mol cupric sulfate and
3.50 $\mu$mol ferrous sulfate,
in 1 liter distilled $H_2O$.
autoclave
pH 8.6 with pH paper Methods for isolating and growing the bacterial strain of the present invention:
3 samples were obtained from an aquarium as follows:
1. 50 ml aquarium water
2. 5 grams of aquarium gravel
3. A strip of a Marineland Aquarium Products BioWheel® filter (a rotating biological contactor).

Each sample was placed in 75 ml of culture mineral medium (see above), with a nitrite concentration at 7mM. They were incubated in the dark at 27° C. in culture flasks with foam stopper and in tissue culture flasks.

Nitrite consumption was measured frequently by the azo dye method. When the nitrite concentration dropped the samples were observed under the microscope, many cell types were seen, in particular rods, cocci packets and spherical, indicating that the culture was not pure.

To obtain a biologically pure culture, successive 10-fold dilutions of a culture known to contain the target organism are made. Generally, 6 to 9 dilutions are made such that the original culture is diluted a million to a billion times. Growth of the nitrite-oxidizing bacteria is then monitored in the dilution cultures. In the case of the present organism, growth and cell division is accessed by measuring the nitrite concentration in the cultures. The nitrite concentration in cultures which contain the nitrite-oxidizing bacteria will decrease over time. Sometimes, a dilution will not exhibit growth (the nitrite concentration will not decrease). This means it was too dilute (no cells present). After a certain amount of time the most diluted sample which exhibited growth of the nitrite-oxidizing bacteria is checked for purity.

This is done by adding a small amount of the dilution to an organic culture media to check for the presence of heterotrophic bacteria as described in Watson and Waterbury 1971 (Watson, S. W. and J. B. Waterbury. 1971. Characteristics of two marine nitrite oxidizing bacteria, *Nitrospina gracilis* nov. gen. nov. sp. and *Nitrococcus mobilis* nov. gen. nov. sp. Arch. Mikrobiol. 77:203–230.). If there is a positive signal such that the culture is still not pure (the solution will become turbid), then that dilution culture is subjected to another series of dilutions and the process repeated until a pure culture is obtained. Once the pure culture is obtained, relatively large number of cells can be grown. These cells can then be preserved in frozen form, freeze dried form or in liquid suspension. Cells for freezing are concentrated from the culture vessel by centrifugation, quick-frozen in a vial placed in a mixture of dry ice and acetone and stored in a laboratory freezer at -80° C. Freeze-drying of microorganisms is accomplished with commercially available bench-top units available from a number of manufacturers, as will be familiar to persons of skill in the art.

In this way, a heterotrophic culture medium can be used to test whether the culture of nitrite-oxidizing bacteria is pure. Only heterotrophic bacteria will grow in this medium (no autotrophic nitrifiers will grow in it). Thus if a sample of nitrite-oxidizing bacteria culture is grown in this medium and it turns cloudy after a day or two, that culture was not pure. This is one means which can be used to test the purity of the isolated bacterial cells; other means will be know to those of skill in the art.

Results

Isolation of putative nitrite-oxidizing bacteria. Two approaches were taken to identify nitrite-oxidizing bacteria in aquarium samples. The first approach was to develop clone libraries from gravel samples from an aquarium at several times during the establishment of vitrification. Samples were taken 17 days and 31 days after the aquarium establishment and ammonia additions started. A third library was constructed from DNA extracted from the material of a commercial biofilter constructed of thermoplastic material (Model CBW-1, Aquaria Inc., Moorpark, Calif.). This filter had been set-up for 109 days in a system with daily dosing of ammonium chloride.

The second approach used to monitor and identify vitrifying microorganisms was denaturing gradient gel electrophoresis (DGGE). The DNA extracted from aquarium gravel samples taken during the establishment of nitrification was subjected to DGGE to produce a pattern of discrete bands. The banding patterns were compared to each other, and to band patterns produced by a mix of known nitrifiers. Unique bands were excised from the gels and sequenced.

The sequences from the clone libraries and DGGE were compared to bacterial sequences found in public databases (BLAST (Altschul, S. F., W. Gish, W. Miller, E. W. Myers, end D. J. Lipman. 1990. Basic local alignment search tool. J. Mol. Biol. 215:403–410) and RDP (Maidak, B. L., N. Larsen, M. J. McCaughey, R. Overbeek, G. J. Olsen, K. Fogel, J. Blandy, and C. R. Woese. 1994. The ribosomal database project. Nucleic Acids Res. 22 3485–3487.). Some sequences, which showed a close similarity to known nitrite-oxidizing organisms, were more completely sequenced.

Identification of putative Nitrospira-like NOB. Five samples were screened for nitrite-oxidizing bacteria by either clone library development or DGGE. A total of 96 clones or excised bands were partially sequenced. Of these, 11 were highly similar to members of the Nitrospira group but none were similar to Nitrobacter spp. The partial sequences were most highly similar to *Nitrospira marina* and *Nitrospira moscoviensis* (data not shown). The 16S rDNA of a representative clone which contained the Nitrospira-like rDNA was fully sequenced, and a phylogenetic tree inferred. Phylogenetic analysis indicated a high similarity between this cloned rDNA (710-9) and members of the Nitrospira group, *Nitrospira moscoviensis* and *Nitrospira marina*. (FIG. 1). The rDNA contained in the clone 710-9 was 96.1% similar to *Nitrospira moscoviensis* and 87.4% similar to *Nitrospira marina* (Table 2).

TABLE 2

Similarity ranking for Clone 710-9 isolated from freshwater aquaria and members of the Nitrospira group.

| | rDNA Source | | | | |
|---|---|---|---|---|---|
| | 710-9 sequence | *Nitrospira moscoviensis* | *Nitrospira marina* | *Leptospirillum sp.* | *Leptospirillum ferroxidans* |
| 710-9 sequence* | | | | | |
| *Nitrospira moscoviensis* | 96.1 | | | | |
| *Nitrospira marina* | 87.4 | 87.6 | | | |
| *Leptospirillum sp.* | 79.9 | 80.3 | 80.2 | | |
| *Leptospirillum ferrooxidans* | 78.1 | 78.4 | 77.9 | 91.0 | |
| *Magnetobacterium bavaricum* | 78.2 | 77.9 | 79.7 | 78.3 | 77.0 |

*positions 24-1284 of 710-9, *E. coli* numbering

Figure 2A:
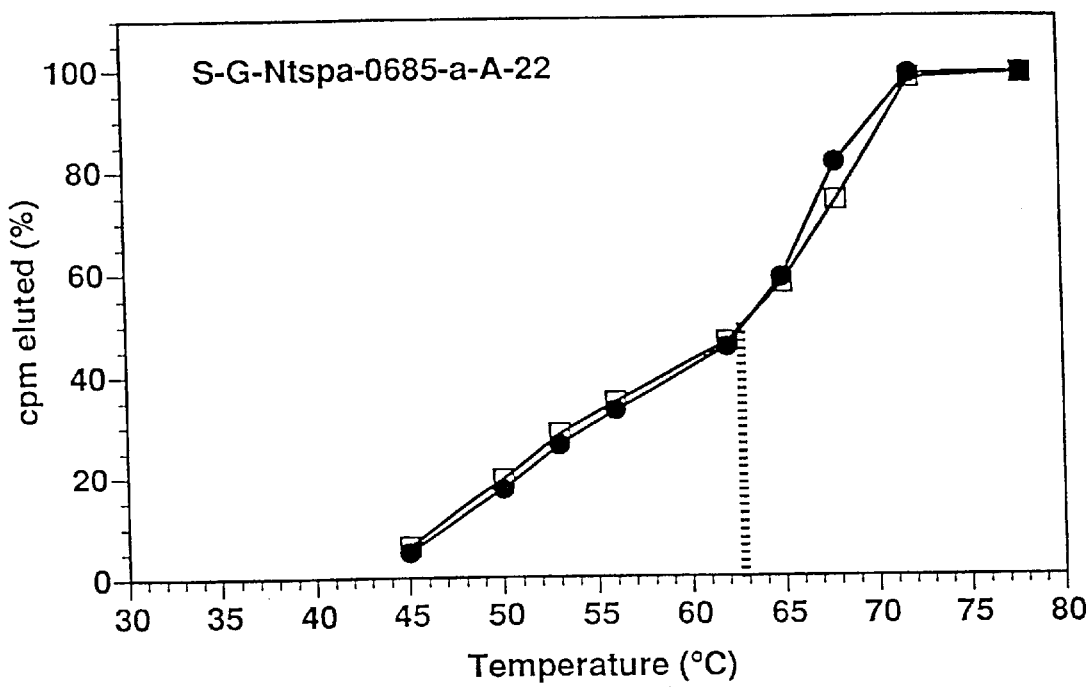
FIGS. 2A and 2B show the results of the temperature dissociation experiments for the probes S-G-Ntspa-0685-a-A-22 and S-*-Ntspa-0454-a-A-19 with the 50% dissociation temperature marked by the vertical line. rRNA of *Nitrospira marina* (□), and transcribed RNA of Clone 710-9 (●, ○).
Figure 2B:
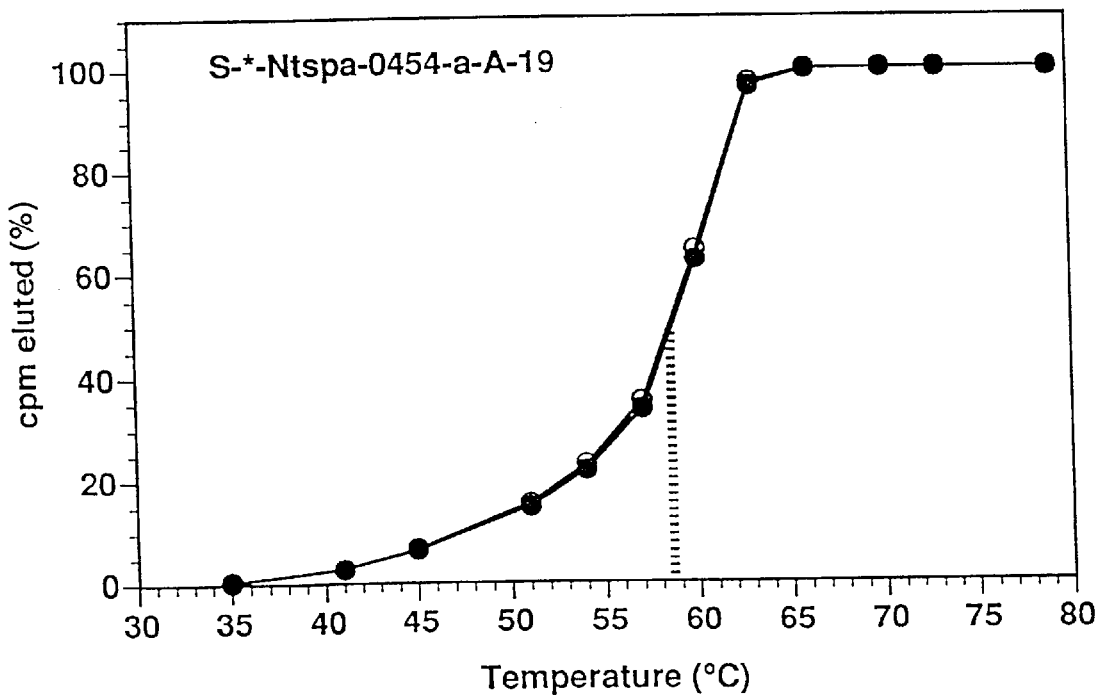

Oligonucleotide probe specificity. Oligonucleotide probe sequences, position (*E. coli* numbering), dissociation temperature Tds, wash temperature, and target groups for the probes are shown in Table 1. For the probe S-*-Ntspa-0454-a-A-19, the Td was 58.5° C., while the Td was 63.0° C. for the S-G-Ntspa-0685-a-A-22 probe (FIG. 2).

Slot blot experiments confirmed that the probe S-G-Ntspa-0685-a-A-22 was specific to the known NOB of the Nitrospira group, as well as the clone 710-9 (FIG. 3). As predicted, probe S-*-Ntspa-0454-a-A-19 hybridized to clone 710-9, but not *Nitrospira marina*. Further, experiments demonstrated that neither probe hybridized with nitrite-oxidizing bacteria which are members of the α or δ subdivisions of the Proteobacteria (FIG. 3).

Detection of NOB in aquaria. Table 3 summarizes the results from the probing of several aquaria biofilms with the NOB probes. Probe S-G-Ntspa-0685-a-A-22 yielded a positive signal with all freshwater and saltwater aquaria tested. The probe S-*-Ntspa-0454-a-A-19 detected Nitrospira-like bacteria in all freshwater aquaria, but not all the saltwater aquaria (Table 3). There were no cases of positive detection by a probe which targets α Proteobacterial Nitrobacter species.

TABLE 3

Results of probing rRNA extracted from aquarium biofilms with nucleic acid probes for nitrite-oxidizing bacteria.

| | | | | | Oligonucleotide Probe[E,F] | | | |
|---|---|---|---|---|---|---|---|---|
| | | | | | Nitrite-oxidizing bacteria (NOB) | | | |
| Sample Label | Aquarium Environment[A] | Biofilm Substrate[B] | Daily Ammonia Amount[C] | Ammonia Source[D] | S-D-Bact -0338-a-A-18 | -S-*-Nbac -1017-a-A-20 | S-G-Ntspa -0685-a-A-22 | S-*-Ntspa -0454-a-A-19 |
| 710r | Freshwater | Polyfiber | 32.1 mM | NH$_4$Cl | + | − | + | + |
| 711r | Freshwater | Polyfiber | 32.1 mM | NH$_4$Cl | + | − | + | + |
| T825 | Freshwater | Polypp | 0.8 g | Fish | + | − | + | + |
| T825 | Freshwater | Gravel | 0.8 g | Fish | + | − | + | + |
| WDF1036 | Freshwater | Polypp | 3.2 g | Fish | + | − | + | + |
| WDF1036 | Freshwater | Gravel | 3.2 g | Fish | + | − | + | + |
| WDF1026 | Freshwater | Polypp | 2.0 g | Fish | + | − | + | + |
| WDF1039 | Freshwater | Gravel | 3.2 g | Fish | + | − | + | + |
| WDF1038 | Freshwater | Sponge | 2.0 g | Fish | + | − | + | + |
| WDF1035 | Freshwater | Polypp | 2.0 g | Fish | + | − | + | + |
| FLRT6 | Freshwater | Gravel | 2.0 g | Fish | + | − | + | + |

TABLE 3-continued

Results of probing rRNA extracted from aquarium biofilms with nucleic acid probes for nitrite-oxidizing bacteria.

| Sample Label | Aquarium Environment[A] | Biofilm Substrate[B] | Daily Ammonia Amount[C] | Ammonia Source[D] | Oligonucleotide Probe[E,F] Nitrite-oxidizing bacteria (NOB) | | | |
|---|---|---|---|---|---|---|---|---|
| | | | | | S-D-Bact -0338-a-A-18 | -S-*-Nbac -1017-a-A-20 | S-G-Ntspa -0685-a-A-22 | S-*-Ntspa -0454-a-A-19 |
| EXP8B | Freshwater | Polypp | 1.4 g | Fish | + | − | + | + |
| FWSW4 | Freshwater | Polypp | 5 mM | NH$_4$Cl | + | − | + | + |
| FWSW6 | Freshwater | Polypp | 5 mM | NH$_4$Cl | + | − | + | + |
| BC2-8 | Freshwater | Gravel | 5 mM | NH$_4$Cl | + | − | + | + |
| BC2-10 | Freshwater | Gravel | 5 mM | NH$_4$Cl | + | − | + | + |
| BC2-12 | Freshwater | Gravel | 5 mM | NH$_4$Cl | + | − | + | + |
| BC2-13 | Freshwater | Gravel | 5 mM | NH$_4$Cl | + | − | + | + |
| BC2-16 | Freshwater | Gravel | 5 mM | NH$_4$Cl | + | − | + | + |
| BC2-4 | Freshwater | Gravel | 2.0 g | Fish | + | − | + | + |
| BC2-16a | Freshwater | Gravel | 2.0 g | Fish | + | − | + | + |
| 714r | Seawater | Polyfiber | 714 mM | NH$_4$Cl | + | − | + | − |
| 715r | Seawater | Polyfiber | 714 mM | NH$_4$Cl | + | − | + | + |
| FWSW2 | Seawater | Polypp | 5 mM | NH$_4$Cl | + | − | + | − |
| FWSW3 | Seawater | Polypp | 5 mM | NH$_4$Cl | + | − | + | − |
| FWSW8 | Seawater | Polypp | 5 mM | NH$_4$Cl | + | − | + | − |
| FWSW9 | Seawater | Polypp | 5 mM | NH$_4$Cl | + | − | + | − |

[A]The type of aquarium water.
[B]The media from which the bacteria cells were extracted; Polypp-polypropylene
[D]fish means the aquarium had a fish population and ammonia was generated by the fish; 'NH4Cl' means that there were no fish in the tank and the ammonia was from daily dosing of ammonium chloride.
[C]values in grams represent the amount of fish feed put into the aquarium each day; values in M or mM are the amount of ammonia dosed to the aquarium or system in which the biofilter was located each day.
[E]+, signal detected by probe; −, no signal detected
[F]A-*-Nbac-1017-a-A-20 was originally called NBAC2 (Hovanec and DeLong 1996) targeting Nitrobacter winogradskyi and Nitrobacter agilis.
S-G-Ntspa-0685-a-A-22 probe targets Nitrospira marina, *Nitrospira moscoviensis* and the Clone 710–9
S-*-Ntspa-0454-a-A-19 probe targets *Nitrospira moscoviensis* and the Clone 710–9

Figure 4A:
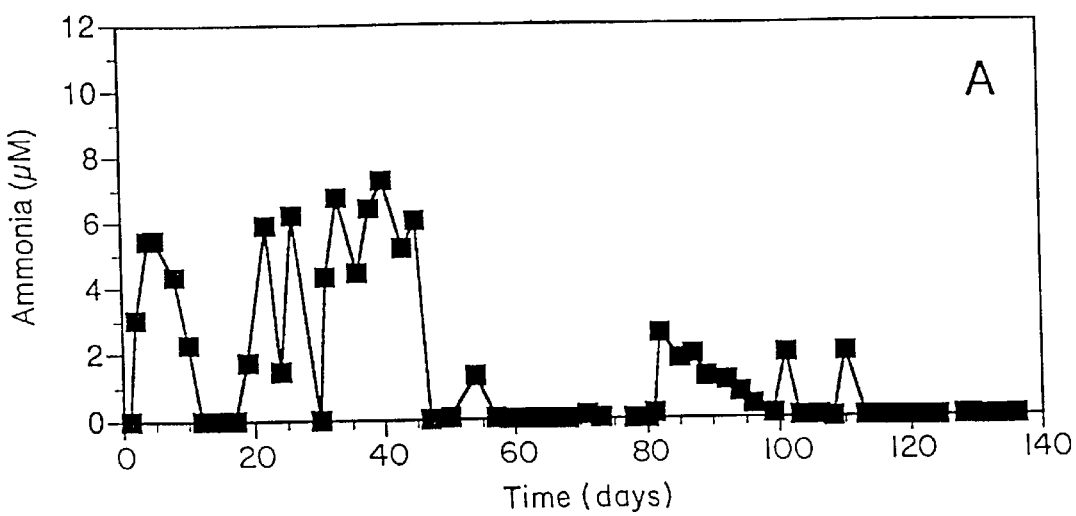
FIGS. 4A–4C show ammonia (A), nitrite (B) and nitrate (C) chemistry for an aquarium from start-up through 138 days. The saw-toothed pattern for ammonia is the result of the increasing frequency of dosing with ammonium chloride as nitrification was being established. The water was switched from fresh to seawater on day 80.
Figure 4B:
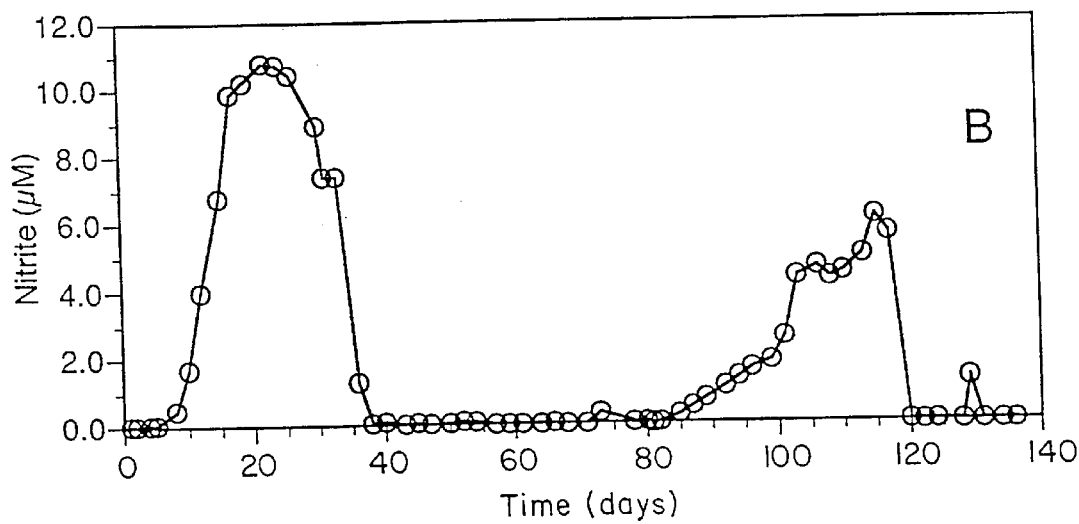
Figure 4C:
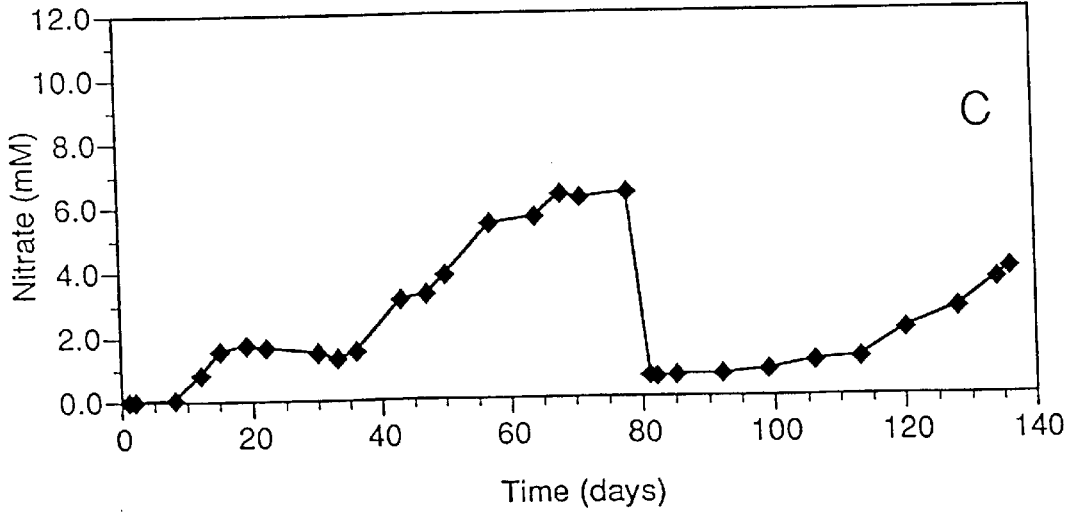

Time series. The ammonia, nitrite and nitrate values for a representative test aquarium dosed with ammonium chloride for 138 days are shown in FIG. 4. The data show the expected pattern for the establishment of nitrification in aquaria. Initially ammonia increased, then decreased to undetectable levels by day 12 (the saw-toothed pattern of the ammonia values is the result of the increasing frequency of ammonia additions). By day 12, nitrite was increasing, reaching its maximum value on day 22. By day 38, nitrite was essentially zero and nitrate was steadily increasing (FIG. 4). The change from freshwater to seawater at day 80 resulted in an immediate increase in ammonia and, subsequently, nitrite. It took nearly 20 days for ammonia oxidation to become re-established. Re-establishment of nitrite oxidation took approximately 40 days.

A DGGE profile for selected days over the first 101 days for this same aquarium shows that the Nitrospira-like rDNA sequence appeared faintly on day 15, corresponding to the onset of nitrite-oxidation (FIG. 5). By day 22 the band corresponding to the Nitrospira-like rDNA sequence increased in relative intensity, and remained intense over the next two sampling dates. After the switch to seawater, the relative intensity of the Nitrospira-like band diminished. The general band pattern also changed qualitatively between freshwater and seawater sampling dates. The banding pattern for day 87 (7 days after the switch) appeared to more closely resemble the pattern for day 57 (freshwater), than the pattern for day 101 (seawater) (FIG. 5).

Figure 6A:
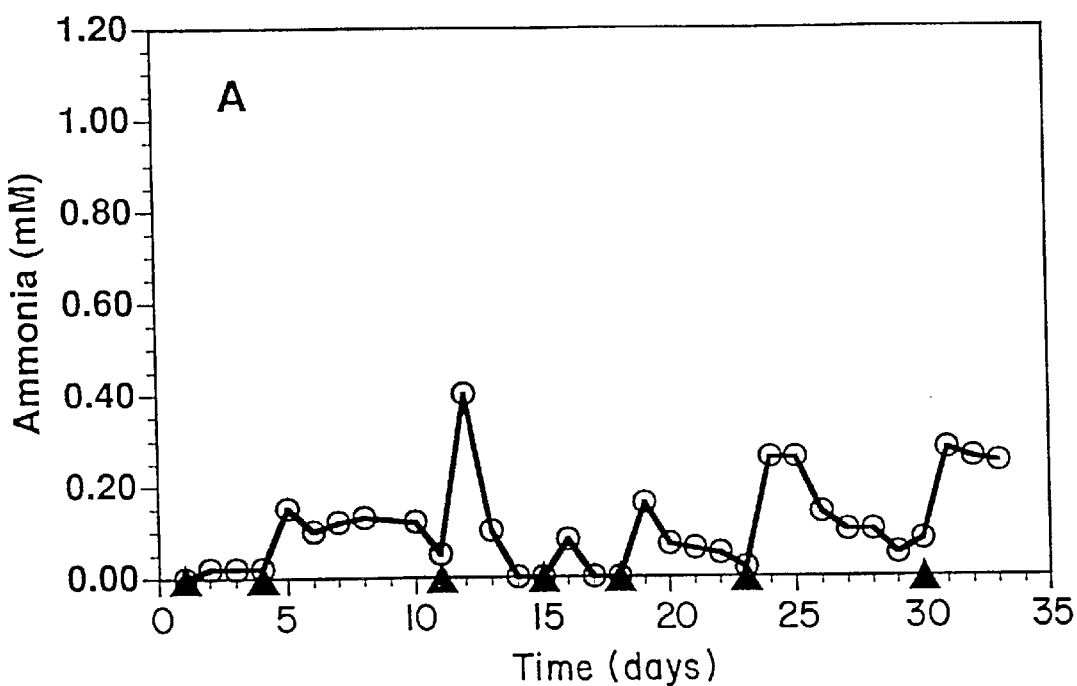
FIGS. 6A and 6B show inorganic nitrogen values for a newly established freshwater aquarium dosed with ammonium chloride over 33 days. (A): Ammonia (○) values along with dates of ammonium chloride additions (▲). (B): Nitrite (□) and nitrate (●) values for the same aquarium. A DGGE profile of the nitrifying assemblage associated with this aquarium is presented in FIG. 7.
Figure 6B:
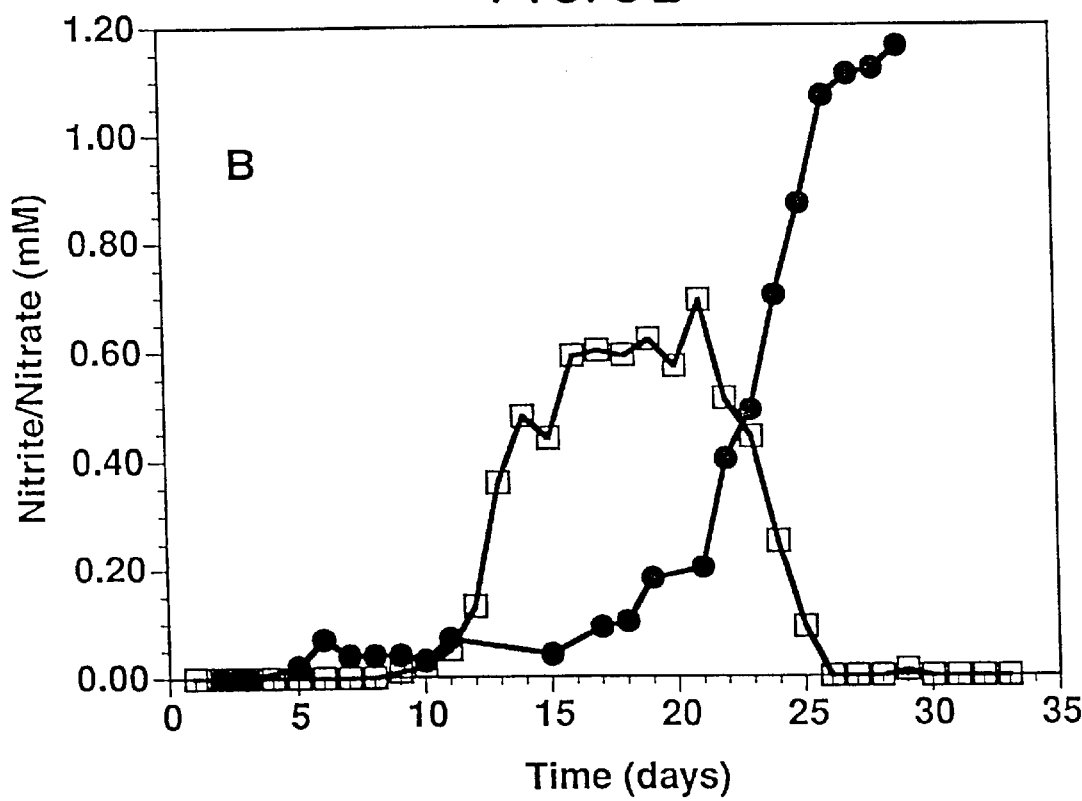
Figures 7A, 7B:
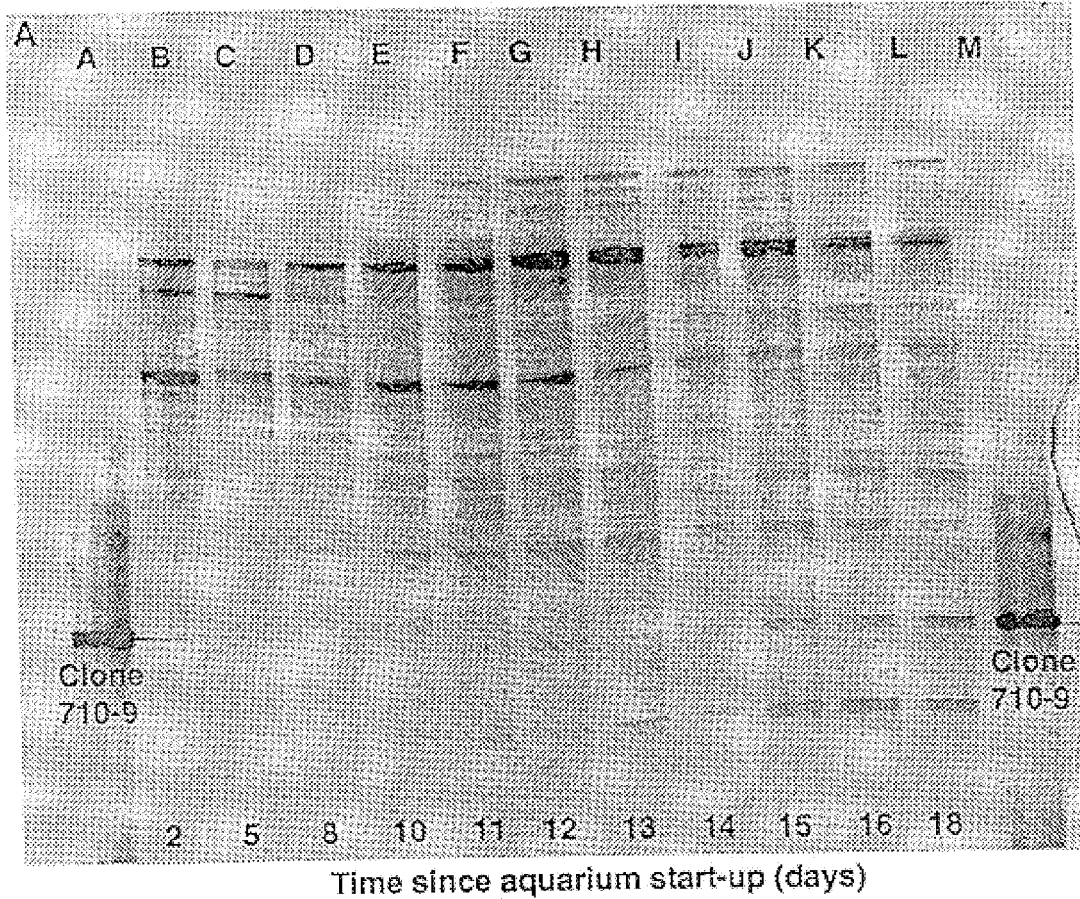
FIG. 7A shows denaturing gradient gel electrophoresis (DGGE) of select dates during the first 18 days after the start-up of a freshwater aquarium during which time nitrification is becoming established. Clone 710-9, a Nitrospira-like putative nitrite-oxidizing bacterium, can be seen to appear starting about day 12 (Lane G).
FIG. 7B shows the relative intensity of the band for clone 710-9 at each sampling date. Associated water chemistry data for this aquarium is presented in FIG. 6.

Time of Nitrospira-like bacterial appearance. The daily concentrations of ammonia, nitrite and nitrate over the first 33 days after set-up of a new aquarium 27 are presented in FIG. 6. The trends are as expected with ammonia peaking about day 12. Nitrite values increased starting at day 12, peaked at day 21, and decreased to below detection limits by day 26. Nitrate steadily increased from about day 15 onwards. DGGE showed that the band corresponding to clone 710-9, the putative NOB, first appeared on day 12 with the relative intensity of the 710-9 band increasing daily based on relative fluorescence units of rDNA amplicons (FIG. 7).

Commercial Additive.

Figure 8A:
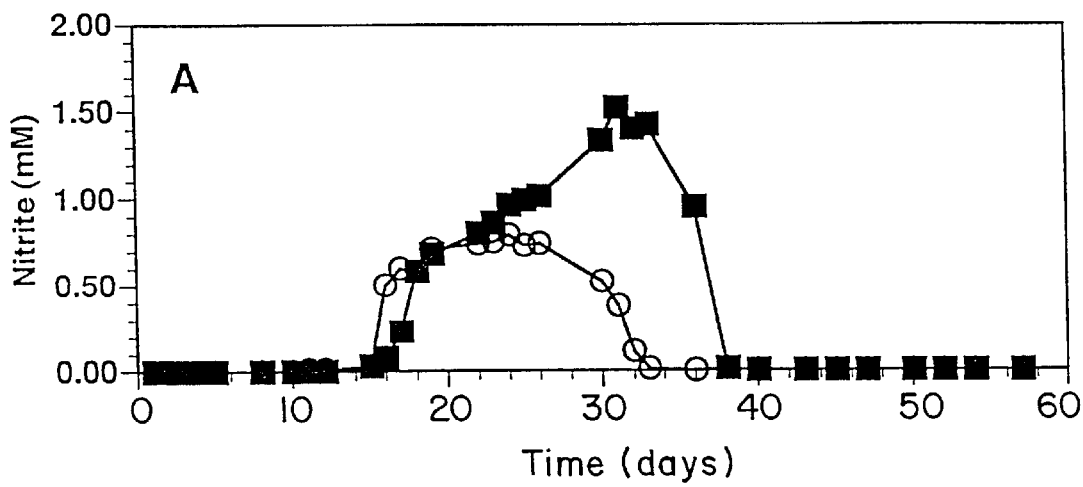
FIGS. 8A–8C show water chemistry data and nucleic acid probe hybridization results for a freshwater aquarium during the first 57 days after start-up. Nitrite (A) and nitrate (B) are for two tanks: Tank 4 (■) which did not receive a commercial bacterial mixture and Tank 16 (○) which received weekly additions of a commercial bacterial mixture (CYCLE®, Rolf C. Hagen Corp., Mansfield, Mass. 02048, USA) for the first 4 weeks. (Nitrate data not obtained for days 18 through 40.) (C) Percent hybridization (relative to that of an eubacterial probe, S-D-Bact-0338-a-A-18) to probes specific for nitrite-oxidizing bacteria (NOB). Probes S-G-Ntspa-0685-a-A-22 and S-*-Ntspa-0454-a-A-19 target Nitrospira spp., while probe S-*-Nbac-1017-a-A-20 is for the αproteobacterial subdivision NOB.
Figure 8B:
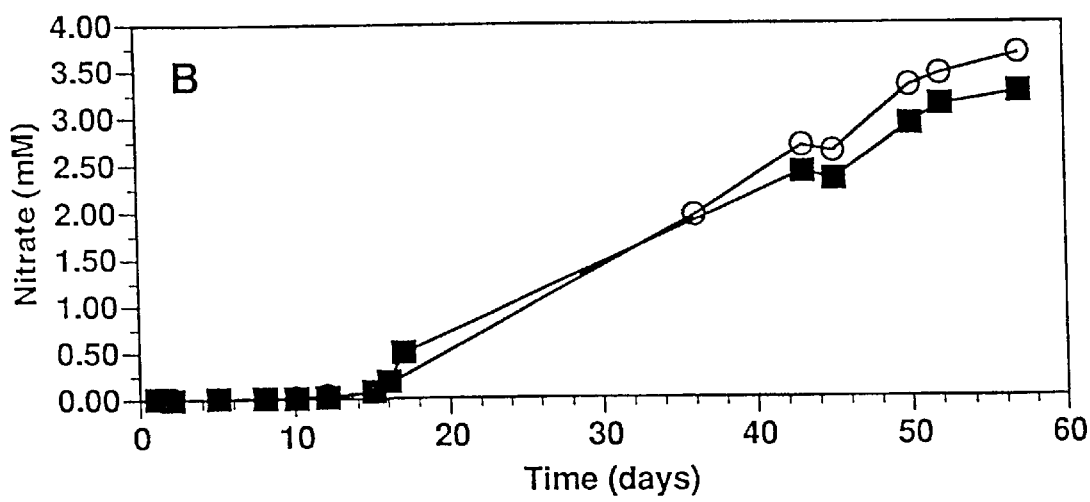
Figure 8C:
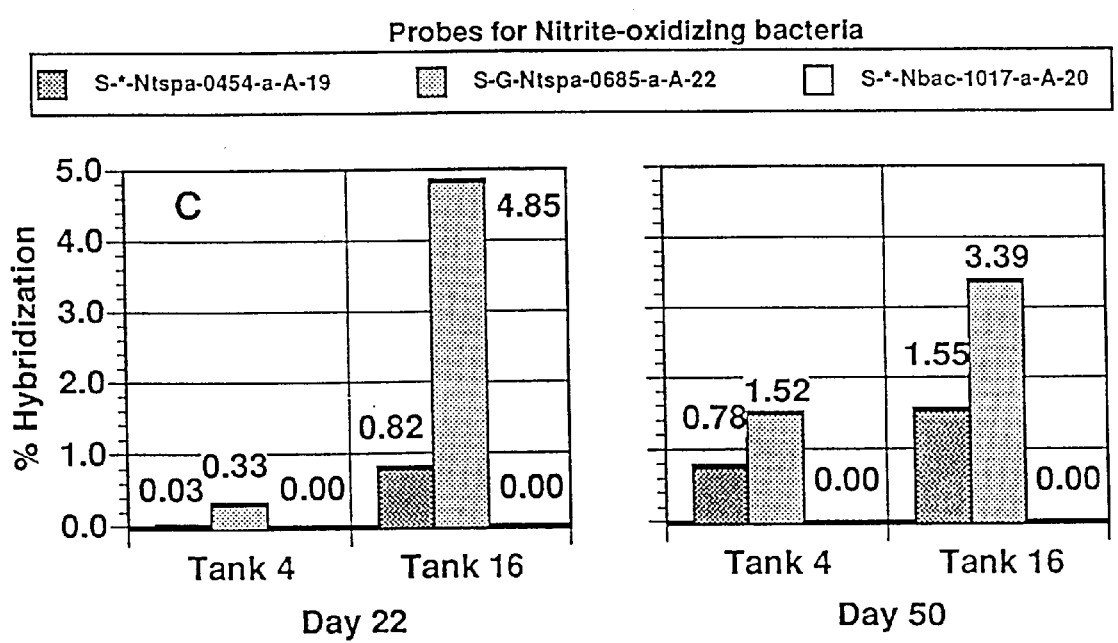

The addition of a commercial bacterial mixture (CYCLE®) which contained Nitrobacter sp., but not Nitrospira sp., did not result in the detection Nitrobacter species by oligonucleotide probe hybridization experiments (FIG. 8). However, a band which co-migrated with a control derived from pure Nitrobacter DNA could be detected in the original commercial mixture by DGGE analysis. Nitrospira-like rRNA was readily detected in the aquarium. Nitrospira group specific probes indicated that the tank which received the additive had a significantly greater percentage of the Nitrospira species rRNA (FIG. 8). By day 16, approximately 5% of the eubacterial rRNA hybridized with the general Nitrospira group-specific probe, compared to only 0.33% of the eubacterial rRNA in the tank which did not receive an additive (FIG. 8). By day 50, the values were 3.39% and 1.52% for the additive and non-additive aquaria, respectively (FIG. 8). From these results it can be concluded that the commercial mixture does not promote the growth of *N. winogradskyi*, which it contains, but instead slightly promotes the growth of the Nitrospira-like bacteria by having some type of fertilization effect.

Nitrite concentrations in the two aquaria decreased as the relative percentage of Nitrospira-like rRNA increased. By day 22, nitrite had reached a maximum in the tank which received the additive. Nitrite concentrations reached maxima in the non-additive aquarium on about day 32. By day 38, the nitrite levels in both aquaria were essentially below our limits of detection, and nitrate levels were equivalent in the treated and non-treated aquaria (FIG. 8).

The results from DGGE analysis, rRNA probing, and sequencing strongly indicate that a Nitrospira-like bacterium is responsible for nitrite oxidation in freshwater aquaria. The combined use of molecular phylogenetic techniques and monitoring of water chemistry suggested a correspondence between changes in the biofilm microbial community which coincided with the onset of ammonia and nitrite oxidation. The commencement of nitrite-oxidation coincided with the appearance of the putative nitrite-oxidizing Nitrospira-like bacterium.

The results lend support to the conclusion of an earlier study (Hovanec and DeLong 1996), which suggested α subdivision Proteobacterial nitrite-oxidizing bacteria (Nitrobacter types) were not major components of nitrite oxidation bacterial populations in freshwater or marine aquaria.

Results regarding the beneficial effects of the addition of a bacterial additive containing Nitrobacter species were equivocal. While nitrite levels dropped earlier in treated aquaria than non-treated aquaria, there was no evidence that Nitrobacter species were actively growing in these aquaria. The fact that Nitrospira-like bacteria were readily detected, and their establishment coincided with nitrite oxidation, supports the conclusion that Nitrospira-like organisms, and not Nitrobacter species, are the major nitrite-oxidizers in the freshwater aquarium environment. It is possible that the addition of bacterial mixtures may supply vitamins and other nutrients which generally stimulate the growth of the nitrifying assemblages, fostering their growth and development, and indirectly stimulating nitrite oxidation.

The foregoing is meant to illustrate, but not limit, the scope of the invention. Indeed, those of ordinary skill in the art can readily envision and produce further embodiments, based on the teachings herein, without undue experimentation.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A method for detecting and determining the quantity of bacteria that oxidize nitrite to nitrate in a media, wherein the 16S rDNA of the bacteria has a nucleotide sequence of SEQ ID NO:1, said method comprising the steps of:
   (a) providing a detectably labeled probe selected from the group consisting of SEQ ID NO: 2 and SEQ ID NO: 3;
   (b) isolating total DNA from the media;
   (c) exposing the isolated total DNA to the detectably labeled probe under conditions under which the probe hybridizes to only the nucleic acid of bacteria having 165 r DNA that has a nucleotide sequence of SEQ ID.NO. 1; and
   (d) detecting and measuring the amount of hybridized probe, wherein the presence of hybridized probe is indicative of the presence of bacteria that oxidize nitrite to nitrate and the amount of hybridized probe is indicative of the quantity of said bacteria that oxidize nitrite to nitrate in said media.

2. The method of claim 1, wherein the media is aquarium water.

3. The method of claim 2, wherein the media includes a material selected from the group consisting of aquarium gravel, filter sponges, filter floss, and plastic filter media.

4. The method of claim 3, wherein the total DNA is isolated from the material selected from the group consisting of aquarium gravel, filter sponges, filter floss, and plastic filter media.

* * * * *

SEQUENCE LISTING

<160> NUMBER OF SEQ ID NOS: 7

<210> SEQ ID NO 1
<211> LENGTH: 1654
<212> TYPE: DNA
<213> ORGANISM: Nitrospira sp.

<400> SEQUENCE: 1

```
ttgggccctc tagatgcatg ctcgagcggc cgccagtgtg atggatatct gcagaattcg    60
gcttagagtt tgatcctggc tcagaacgaa cgctggcggc gcgcctaata catgcaagtc   120
gagcgagaag gtgtagcaat acacttgtaa agcggcgaac gggtgaggaa tgcatgggta   180
acctaccctc gagtggggaa taactagccg aaaggttagc taataccgca tacgcttccg   240
ggacttcggt tccggaagga aagcaatacc gtgggtattg cgctcatgga tgggctcatg   300
tcctatcagc ttgttggtga ggtaacggct caccaaggct tcgacgggta gctggtctga   360
gaggacgatc agccacactg gcactgcgac acgggccaga ctcctacggg aggcagcagt   420
aaggaatatt gcgcaatgga cgaaagtctg acgcagcgac gccgcgtggg ggatgaaggt   480
cttcggattg taaaccccct tcgggaggga agatggagtg ggtaaccact tggacggtac   540
ctccagaagc agccacggct aacttcgtgc cagcagccgc ggtaatacga aggtggcaag   600
cgttgttcgg attcactggg cgtacagggg gcgtaggcgg ttaggtaagc cctccgtgaa   660
atctccgggc ctaacccgga aagtgcagag gggactgctt ggctagagga tgggagagga   720
gcgcggaatt cccggtgtag cggtgaaatg cgtagagatc gggaggaagg ccggtggcga   780
aggcggcgct ctggaacatt actgacgctg aggctcgaaa gcgtgggga gcaaacagga   840 ttagataccc tggtagtcca cgccttaaaa ctatggatac taagtgtcgg cggtttaccg   900
ccggtgccgc astaacgcaa taagtatccc gcctgggaag tacggccgca aggttgaaac   960
tcaaaggaat tgacgggggc ccgcacaagc ggtggagcat gtggtttaat tcgacgcaac  1020
gcgaagaacc ttacccaggc tggacatgca ggtagtagaa gggtgaaagc ctaacgaggt  1080
agaaatacca tcctgctcag gtgctgcatg gctgtcgtca gctcgtgccg tgaggtgttg  1140
```

```
ggttaagtcc cgcaacgagc gcaaccctg tcttcagtta ctaacaggtc aagctgagaa    1200
ctctggagag actgcccagg agaacgggga ggaaggtggg gatgacgtca agtcagcatg   1260
gcctttatgc ctggggctac acacgtgcta caatggccgg tacaaagggc tgcaaacccg   1320
cgagggggga gccaatccca aaaaaccggc ctcagttcag attgggtct gcaactcgac    1380 cccatgaagg cggaatcgct agtaatcgcg gatcagcacg ccgcggtgaa tacgttcccg   1440
ggccttgtac acaccgcccg tcacaccacg aaagtttgtt gtacctgaag tcgttgygcc   1500
aaccgcaagg aggcaggcgc ccacggtatg accgatgatt ggggtgaagt cgtaacaagg   1560
taaccaagcc gaattccagc acactggcgg ccgttactag tggatccgag ctcggtacca   1620
agcttgatgc atagcttgag tattctatag tgtc                                1654
```

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 2
caccgggaat tccgcgctcc tc                                              22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 3
tccatcttcc ctcccgaaaa                                                 20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
gtttgatcct ggctcag                                                    17

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5
ggttaccttg ttacgactt                                                  19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

```
<400> SEQUENCE: 6
gwattaccgc ggckgctg                                                    18

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 7
cctacgggag gcagcag                                                     17
```